(12) United States Patent
Schlenoff

(10) Patent No.: US 9,352,068 B2
(45) Date of Patent: May 31, 2016

(54) BIOCOMPATIBLE POLYELECTROLYTE COMPLEXES AND METHODS OF USE

(71) Applicant: Florida State University Research Foundation, Inc., Tallahassee, FL (US)

(72) Inventor: Joseph B. Schlenoff, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 14/602,628

(22) Filed: Jan. 22, 2015

(65) Prior Publication Data

US 2015/0140055 A1 May 21, 2015

Related U.S. Application Data

(63) Continuation of application No. 13/391,312, filed as application No. PCT/US2010/045955 on Aug. 19, 2010, now Pat. No. 9,005,662.

(60) Provisional application No. 61/235,554, filed on Aug. 20, 2009, provisional application No. 61/236,616, filed on Aug. 25, 2009.

(51) Int. Cl.
| | |
|---|---|
| *A61L 15/60* | (2006.01) |
| *A61L 15/44* | (2006.01) |
| *A61L 15/24* | (2006.01) |
| *A61L 15/42* | (2006.01) |

(52) U.S. Cl.
CPC .............. *A61L 15/60* (2013.01); *A61L 15/24* (2013.01); *A61L 15/42* (2013.01); *A61L 15/425* (2013.01); *A61L 15/44* (2013.01); *A61L 2300/216* (2013.01); *A61L 2300/404* (2013.01); *A61L 2300/406* (2013.01); *A61L 2300/408* (2013.01); *A61L 2300/41* (2013.01); *A61L 2300/412* (2013.01); *A61L 2300/414* (2013.01); *A61L 2300/418* (2013.01); *A61L 2300/42* (2013.01); *A61L 2300/43* (2013.01)

(58) Field of Classification Search
USPC ............................................... 521/55
See application file for complete search history.

(56) References Cited

U.S. PATENT DOCUMENTS

| | | | | |
|---|---|---|---|---|
| 4,008,353 | A * | 2/1977 | Gross ................... | C08F 8/00 427/385.5 |
| 6,667,424 | B1 * | 12/2003 | Hamilton ............... | A61F 13/15 604/360 |
| 2003/0175517 | A1 | 9/2003 | Voigt et al. | |
| 2004/0009210 | A1 | 1/2004 | Koenig et al. | |
| 2005/0054784 | A1 | 3/2005 | Qin et al. | |
| 2005/0152955 | A1 | 7/2005 | Akhave et al. | |
| 2005/0208100 | A1 | 9/2005 | Weber et al. | |
| 2005/0287111 | A1 | 12/2005 | Schlenoff et al. | |
| 2009/0149948 | A1 | 6/2009 | Atanasoska et al. | |
| 2009/0162640 | A1 | 6/2009 | Schlenoff | |

OTHER PUBLICATIONS

Jaber, Jad A., et al, Mechanical Properties of Reversibly Cross-Linked Ultrathin Polyelectrolyte Complexes, Journal of American Chemical Society; Feb. 10, 2006, pp. 2940-2947, vol. 128, No. 9.
International Search Report and Written Opinion of the International Searching Authority mailing on Oct. 15, 2010 regarding PCT/us2010/045955 filed on Aug. 19, 2010, 9 pgs.

\* cited by examiner

*Primary Examiner* — Walter Webb
(74) *Attorney, Agent, or Firm* — Armstrong Teasdale LLP

(57) ABSTRACT

An article comprising a polyelectrolyte complex comprising an interpenetrating network of at least one predominantly positively charged polyelectrolyte polymer and at least one predominantly negatively charged polyelectrolyte polymer, the polyelectrolyte complex further comprising a plurality of closed-shell pores, the plurality of pores having at least one average transverse dimension between about 100 nanometer and about 1000 micrometers.

30 Claims, 7 Drawing Sheets

BIOCOMPATIBLE POLYELECTROLYTE COMPLEXES AND METHODS OF USE

CROSS REFERENCE TO RELATED APPLICATIONS

This application is a continuation application of U.S. application Ser. No. 13/391,312, which was filed Feb. 20, 2012. U.S. application Ser. No. 13/391,312 claims priority from International Application No. PCT/US2010/045955, which was filed on Aug. 19, 2010. International Application No. PCT/US2010/045955 claims priority from U.S. provisional application Ser. No. 61/235,554, which was filed Aug. 20, 2009, and from U.S. provisional application Ser. No. 61/236,616, which was filed Aug. 25, 2009.

STATEMENT REGARDING FEDERALLY SPONSORED RESEARCH OR DEVELOPMENT

This invention was made with Government support under Grant No. DMR 0309441 awarded by the National Science Foundation. The Government has certain rights in the invention.

FIELD OF THE INVENTION

The present invention relates to articles comprising a polyelectrolyte complex and a plurality of closed shell micropores and their use as materials for protecting wounds.

BACKGROUND OF THE INVENTION

Hydrogels comprise water and polymers and are useful for medical and pharmaceutical applications (e.g. see Peppas, N. A.; Editor, *Hydrogels in Medicine and Pharmacy, Vol. 3: Properties and Applications*. CRC Press Boca Raton 1987; p 195 pp.). Hydrogels are usually held together via physical or chemical crosslinks, otherwise the polymers of which they are comprised would dissolve in the solvent (water). Polyelectrolyte complexes are interpenetrating complexes of one or more predominantly positive polyelectrolytes and one or more predominantly negative polyelectrolytes. The opposite charges on the polymers form ion pairs between chains, holding the chains together. This ion pairing is a type of physical crosslinking. Polyelectrolyte complexes in contact with aqueous solutions can be considered hydrogels with high crosslinking density.

Recent studies have evaluated the static mechanical properties of polyelectrolyte multilayers, which are ultrathin films of complexed polyelectrolytes. See, for example, Jaber, J. A. and Schlenoff, J. B., J. Am. Chem. Soc. 128, 2940-2947 (2006). Polyelectrolyte multilayers are intermolecular blends of positively and negatively charged polyelectrolyte, wherein each layer of polyelectrolyte added to a growing film has an opportunity to complex efficiently and completely with the existing material, excluding the maximum amount of water. The elastic modulus of these films ranges from kPa to MPa. However, these films are far too thin (a few micrometers or less) to be used for mechanical components in most systems. Furthermore, little is known of the dynamic mechanical properties of molecularly blended complexes of positive and negative polyelectrolytes.

There is a need to prepare articles with dimensions in the millimeter to centimeter to meter scale to provide materials and shapes for biomedical and engineering applications. Polyelectrolyte complexes are prepared in a straightforward manner by mixing two or more solutions of positive and negative polyelectrolytes. However, the resulting precipitate is gelatinous and difficult to process. The dried complexes, for example, are generally infusible and therefore cannot be injection molded or formed into articles under elevated temperatures. Michaels (U.S. Pat. No. 3,324,068) has disclosed the used of non-volatile plasticizers such as nonvolatile acids, organic oxysulfur compounds and organic oxyphosphorus compounds to decrease the brittleness of nonporous polyelectrolyte complexes when they are dried. U.S. Pat. No. 3,546,142 describes a method for creating solutions of polyelectrolyte complexes using aggressive ternary solvents which are mixtures of salt, water and organic solvent. Said solutions of complexes may be formed into nonporous solids by diluting the solution, or by evaporating the solvent (film casting). Mani et al. (U.S. Pat. No. 4,539,373) point out that the solid complexes "are not thermoplastic, i.e. they are not moldable or extrudable, so they must be handled as solutions." Mani et al. disclose a nonporous polyelectrolyte complex comprising thermoplastic repeat units which can be thermally molded.

One of the many biomedical applications of hydrogels is as materials for wound protection or dressing. However, the brittle nature of polyelectrolyte complexes prevents them from conforming efficiently to the wound or limb when they are used for wound dressing. Effing (U.S. Pat. No. 6,936,746) recognized that "absorbers of this kind on a polyelectrolyte base are hard and brittle because of their high salt content and their crosslinking in the solid state." Thus, U.S. Pat. No. 6,936,746 discloses a wound dressing comprising fibers and polyelectrolyte complexes which has adequate mechanical stability. In order to impart supporting or load-bearing properties to the dressing the fibrous complex had to be further applied to carrier materials.

U.S. Pub. No. 2009/0162640, which is incorporated fully by reference, describes fully hydrated (i.e. complexes in contact with water) polyelectrolyte complexes may be formed into shapes without the addition of organic solvent, and without the need for dissolution, if they are doped with salt ions to a sufficient extent.

In many cases, porosity within a gel is desired. Said pores are of micrometers in diameter. Open shell pores are not isolated from each other by a shell wall and are thus interconnected. Liquid may flow freely from one pore to another. In the open-shell pore architecture, liquid may flow through an entire article without having to traverse solid material. Open shell pores are useful as supports for cell growth in tissue engineering for transporting nutrients to cells. Sponges have open shell pores. Closed shell pores are not interconnected, and liquid must permeate through a shell wall to enter another pore. It is possible to trap species in closed shell pores if said species are not able to permeate through the material that comprises the wall.

Vibrations in mechanical systems can have adverse consequences, such as fatigue, failure, and noise. Vibration suppression is achieved by passive or active methods. While active methods reduce vibrations in real time by making use of sensors and actuators, passive methods exploit the inherent ability of viscoelastic materials such as polymers to absorb and dissipate vibration energy.

Mechanical damping materials remove energy from a system. Motions to be damped can be periodic and regular (e.g., sine wave, square wave) or they can be irregular. Often a single mechanical event must be damped. Such an event is termed a shock, and the mechanical damping is termed shock absorption. Most damping measurements apply a periodic deformation to the article being tested, but it is also possible to assess the damping characteristics of a material from a single shock.

Damping or shock-absorbing properties are not determined from static measurements. Damping properties are ascertained by time varying or periodic deformation of the sample. Thus, a soft material (low E) is not necessarily a good candidate for damping. Furthermore, a material that is effective for damping over a certain frequency range may not be effective for damping over another frequency range. Therefore, in reporting a complex modulus (E* or G*), a frequency or frequency range is preferably specified.

SUMMARY OF THE INVENTION

Among the various aspects of the present invention may be noted an article comprising a polyelectrolyte complex comprising an interpenetrating network of at least one predominantly positively charged polyelectrolyte polymer and at least one predominantly negatively charged positive polyelectrolyte polymer, the polyelectrolyte complex further comprising a plurality of stable closed-shell pores. The plurality of pores typically has at least one average transverse dimension between about 100 nanometers and about 1000 micrometers, preferably between about 1 micrometer and about 100 micrometers. The pores may comprise water and, optionally, additional large and/or small molecules and/or particles. In one preferred embodiment, the majority of said pores are non-interconnecting.

In one embodiment, the article is formed by forcing a material comprising a salt-doped blend of interpenetrating positive and negative polyelectrolyte into a mold under pressure and said article adopts and maintains the contours of the mold following release from the mold.

In another embodiment, the article is formed by forcing a material comprising a salt-doped blend of interpenetrating positive and negative polyelectrolyte through an orifice, said orifice defining the cross section of the article as it passes through the orifice.

In some embodiments, the article may be introduced into a cavity by pressure injection through a needle of microporous polyelectrolyte complex in the presence of salt. Accordingly, the invention is further directed to a method for replacing the material of an intervertebral disk, the method comprising separating the vertebrae, removing the from 0 to 100% of the existing disk, and injecting microporous polyelectrolyte complex through a needle into the space occupied by the disk.

Said article may be adapted for use in wound dressing or protection. In another aspect of this invention, a wound protection system comprises a sealed container containing said article. When used as a wound protection system article is preferably first activated by exposure to heat, directly or indirectly. The microporous polyelectrolyte complex is then removed from a container, e.g., packaging, and deformed to cover a wound.

In a preferred method of use, the microporous polyelectrolyte complex article is deformed to circumferentially enclose a wounded limb, organ, vessel or broken bone. The complex is sealed back on itself when wet by applying pressure.

In another preferred method of use, after the microporous polyelectrolyte complex article is deformed to cover a wound it is further rinsed with water to remove excess doping salt. Said rinse increases the modulus of the polyelectrolyte complex providing mechanical support.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE EMBODIMENT(S) OF THE INVENTION

Figure 1:
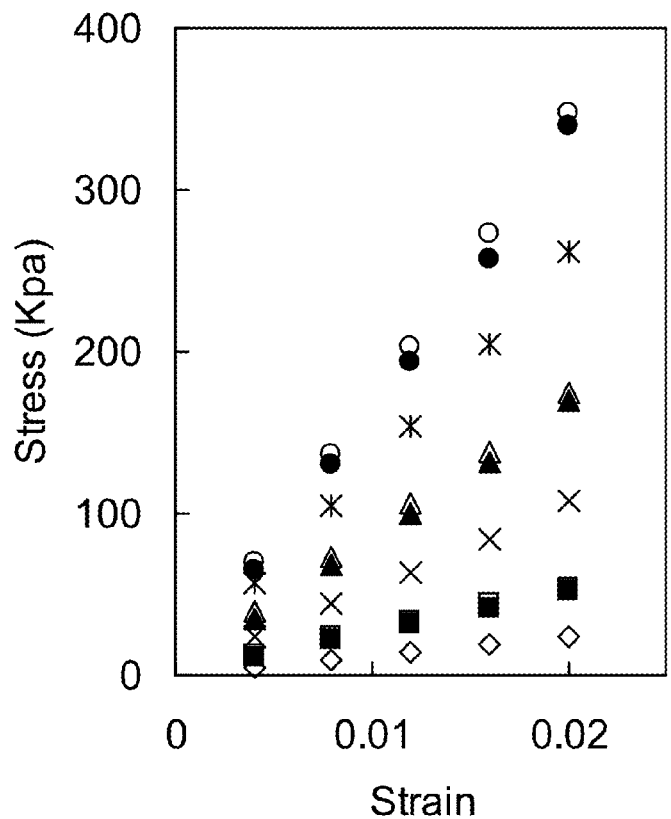
FIG. 1 is a graph depicting the stress-strain curves of a (PDADMA/PSS)$_{250}$@1.0M NaCl multilayer at different salt concentrations. Open circles, asterisk, triangles, crosses, squares and diamonds correspond to the stretching cycle (in increasing order of elongation) with salt concentrations of 0.0, 0.2, 0.4, 0.6, 0.8 and 1.0M NaCl, respectively. Solid circles, triangles and squares indicate a decreasing elongation cycle at 0.0, 0.4, 0.8M. The data in the graph were obtained according to the method of Example 1.

One aspect of the invention is an article comprising a polymer, in particular, a polymer known as a "polyelectrolyte" that comprises multiple electrolytic groups that dissociate in aqueous solutions, making the polymer charged. The article of the present invention comprises a polyelectrolyte complex, that is, an intermolecular blend of at least one predominantly positively charged polyelectrolyte polymer and a predominantly negatively charged polyelectrolyte polymer. The polyelectrolyte complex is preferably compacted, such as by centrifugation or pressure, in a manner that increases the density of the polyelectrolyte complex to a value substantially greater than that which may be obtained following precipitation. Moreover, the article may be formed or shaped to have dimensions typically on the order of millimeters to centimeters, which is also substantially greater than that achievable by conventional multilayering and intermixing methods.

In accordance with one aspect of the present invention, it has been discovered that increasing the salt concentration within the bulk of the fully hydrated polyelectrolyte complex by contacting it with a sufficiently high concentration of salt renders the complex flowable without resorting to a change in temperature or other conditions. Under such flowable conditions the complex may be reshaped into a second persistent shape. Conversely, decreasing the salt concentration within the bulk of the polyelectrolyte complex causes the complex to revert to a non-flowable state. Accordingly, the dynamic mechanical properties of an article comprising the polyelectrolyte complex may be initially controlled by controlling the salt concentration during the preparation of the polyelectrolyte complex and then altered by increasing or decreasing the salt concentration of the solution contacting the article after preparation. Thus, for example, a flowable microporous article may be prepared in the presence of high salt concentration, and then injected into a mold. Once the flowable article is in the mold, or has been removed from the mold, a concentration gradient may be applied by contacting the reshaped article with a solution having a lower salt concentration, which thereby causes salt located in the bulk of the article to diffuse out into the solution, making the microporous article less flowable, thereby causing an increase in the modulus of the article, whose shape is defined by the inner surfaces of the mold.

In general, the polyelectrolyte complex is formed by combining at least one predominantly negatively charged polyelectrolyte polymer and at least one predominantly positively charged polyelectrolyte polymer. In a preferred embodiment, the formation of the article starts with combining separate solutions, each containing one of the polyelectrolytes; in this embodiment, at least one solution comprises at least one predominantly positively charged polyelectrolyte polymer, and at least one solution comprises at least one predominantly negatively charged polyelectrolyte polymer. Either or both or any of these solutions may comprise salt ions or additives. The formation of a polyelectrolyte complex, Pol⁺Pol⁻, by mixing individual solutions of the polyelectrolytes in their respective salt forms, Pol⁺A⁻ and Pol⁻M⁺, may be represented by the following equation:

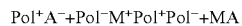

where $M^+$ is a salt cation, such as sodium, and $A^-$ is a salt anion such as chloride. Pol⁻ and Pol⁺ represent repeat units on predominantly negatively charged and predominantly positively charged polyelectrolytes, respectively. According to the equation, the process of complexation releases salt ions into external solution, which are then part of the salt solution concentration.

Separate solutions containing the polyelectrolytes are preferably combined in a manner that allows the positively-charged polyelectrolyte(s) and the negatively-charged polyelectrolyte(s) to intermix. Intermixing the respective polyelectrolytes causes the in situ formation of a polyelectrolyte complex comprising an intermolecular blend of the positively-charged polyelectrolyte polymer and the negatively-charged polyelectrolyte polymer. Preferably, at least two solutions of polyelectrolytes are mixed. Optionally, more than two solutions comprising polyelectrolytes may be mixed, either simultaneously or sequentially. For example, positive polyelectrolyte A in solution 1 may be mixed with negative polyelectrolyte B in solution 2 to give a precipitate. Then, positive polyelectrolyte C in solution 3 may be added. Alternatively, positive polyelectrolytes A and C may be mixed (yielding no precipitate) and then negative polyelectrolyte B may be added. The order of mixing is not trivial and must be optimized on an experimental basis. For the purposes of obtaining as homogeneous a product as possible, the latter method of mixing is preferred. Preferably, at least one of the solutions comprises salt ions, such that salt ions also intermix with and become part of the polyelectrolyte complex. The resulting polyelectrolyte complex may simply be allowed to precipitate and settle to the bottom of the container. The supernatant is, in a preferred embodiment, separated to the extent possible from the polyelectrolyte complex. The precipitate formed after mixing said solutions is gelatinous and of poor structural integrity.

Individual polyelectrolyte solutions that are mixed may themselves comprise mixtures of polyelectrolytes. For example, a solution may comprise two positive polyelectrolytes with two distinct chemical compositions. When the mixture of positive polyelectrolytes is mixed with the negative polyelectrolyte solutions the resulting complex will incorporate a blend of the two positive polyelectrolytes. Such a strategy is described for example in Z. Sui, J. B. Schlenoff, Langmuir vol. 18, p 8263 (2003).

The precipitated polyelectrolyte complex is preferably compacted. In one embodiment, compacting may be accomplished by centrifugation, such that the polyelectrolyte complex is compacted into a plug of material inside the centrifuge vessel. In a preferred embodiment, salt is present during compaction.

Porosity

The article of the present invention comprises a compacted polyelectrolyte complex, the polyelectrolyte complex comprising a plurality of pores. In general, the pores are approximately spherical, but the compaction process may cause the spherical shape to be distorted, such as, for example by elongation caused by strain. An elongated pore may be in the shape of an oblate spheroid or a prolate spheroid.

Pore size: In one preferred embodiment, the plurality or population of pores encapsulated in the polyelectrolyte complex article has at least one average transverse dimension, for example, a diameter, whose length ranges from about 100 nanometers to about 1000 micrometers, such as from about 0.5 micrometers (500 nanometers) to about 1000 micrometers, such as from about 1 micrometer to about 1000 micrometers, preferably from about 1 micrometer to about 100 micrometers, and more preferably from about 5 micrometers to about 100 micrometers. A transverse dimension comprises a distance from a point on one surface of the pore to another point on the opposing surface of the pore. When the pore is a sphere, the transverse dimension is identical to the diameter, this transverse dimension being sufficient to define the shape of the pore. When the pore is elongated, for example a prolate spheroid or an oblate spheroid, the transverse dimension may be either of the major or minor axes, these two transverse dimensions defining the shape of the pore.

Pore size distribution: In a preferred embodiment, the size distribution of the population of pores is preferably narrow. Preferably, no more than 10% of the pores within the population have transverse dimensions less than 10% of the average transverse dimension of the entire population and no more than 10% of the pores have transverse dimensions more than 300% of the mean transverse dimension of the entire population. For example, if the entire population of pores comprises spheres, no more than 10% of the pores within the population have diameters less than 10% of the average transverse dimension of the entire population and no more than 10% of the pores have diameters more than 300% of the mean transverse dimension of the entire population.

Pore interconnectivity: In preferred embodiments, the pore structure of the article is preferably closed shell. That is, pores are not interconnected and each pore is isolated from other pores by means of a pore wall. Preferably greater than 10% of the pores are closed shell. More preferably greater than 50% of the pores are closed shell.

Pore volume: The total percentage volume of the porosity of the article is preferably from about 95 to about 1 percent. More preferably, pores comprised between 10 and 90% of the total volume of the article.

Pore composition: Pores are preferably filled with liquid, preferably water, although other liquids, such as methanol, ethanol or other organic solvents may also be present. Pores may also comprise room temperature ionic liquids as described in Chem. Rev., 2007, 107 (6), pp 2615-2665, including chiral ionic liquids, as described in Science (2003) 302:792 793 and U.S. Pat. No. 6,900,313. Optionally, pores may comprise medication known to assist in the treatment of internal or external wounds, sores, burns, warts, and other maladies of the skin.

Polyelectrolyte Polymers for Complexes

The charged polymers (i.e., polyelectrolytes) used to form the complexes are water and/or organic soluble and comprise one or more monomer repeat units that are positively or negatively charged. The polyelectrolytes used in the present invention may be copolymers that have a combination of charged and/or neutral monomers (e.g., positive and neutral; negative and neutral; positive and negative; or positive, negative, and neutral). Regardless of the exact combination of charged and neutral monomers, a polyelectrolyte polymer of the present invention is predominantly positively charged or predominantly negatively charged and hereinafter is referred to as a "positively-charged polyelectrolyte" or a "negatively-charged polyelectrolyte," respectively.

Alternatively, the polyelectrolytes can be described in terms of the average charge per repeat unit in a polymer chain. For example, a copolymer composed of 100 neutral and 300 positively charged repeat units has an average charge of 0.75 (3 out of 4 units, on average, are positively charged). As another example, a polymer that has 100 neutral, 100 negatively charged, and 300 positively charged repeat units would have an average charge of 0.4 (100 negatively charged units cancel 100 positively charged units leaving 200 positively charged units out of a total of 500 units). Thus, a positively-charged polyelectrolyte has an average charge per repeat unit between 0 and 1 and a negatively-charged polyelectrolyte has an average charge per repeat unit between 0 and −1. An example of a positively-charged copolymer is PDADMA-co-PAC (i.e., poly(diallyldimethylammonium chloride) and polyacrylamide copolymer) in which the PDADMA units have a charge of 1 and the PAC units are neutral so the average charge per repeat unit is less than 1.

Some polyelectrolytes comprise equal numbers of positive repeat units and negative repeat units distributed throughout the polymer in a random, alternating, or block sequence. These polyelectrolytes are termed "amphiphilic" polyelectrolytes. For examples, a polyelectrolyte molecule may comprise 100 randomly distributed styrene sulfonate repeat units (negative) and 100 diallyldimethylammonium chloride repeat units (positive), said molecule having a net charge of zero.

Some polyelectrolytes comprise a repeat unit that has both a negative and positive charge. Such repeat units are termed "zwitterionic" and the polyelectrolyte is termed a "zwitterionic polyelectrolyte." Though zwitterionic repeat units contribute equal number of positive and negative repeat units, the zwitterionic group is still solvated and relatively hydrophilic. An example of a zwitterionic repeat unit is 3-[2-(acrylamido)-ethyldimethyl ammonio]propane sulfonate, AEDAPS. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 10% and about 70% zwitterionic units. Preferred compositions of polyelectrolytes comprising zwitterionic repeat units also comprise between about 10% and about 90% non-zwitterionic charged repeat units.

The charges on a polyelectrolyte may be derived directly from the monomer units, or they may be introduced by chemical reactions on a precursor polymer. For example, PDADMA is made by polymerizing diallyldimethylammonium chloride, a positively charged water soluble vinyl monomer. PDADMA-co-PAC is made by the polymerization of a mixture of diallyldimethylammonium chloride and acrylamide (a neutral monomer which remains neutral in the polymer). Poly(styrenesulfonic acid) is often made by the sulfonation of neutral polystyrene. Poly(styrenesulfonic acid) can also be made by polymerizing the negatively charged styrene sulfonate monomer. The chemical modification of precursor polymers to produce charged polymers may be incomplete and typically result in an average charge per repeat unit that is less than 1. For example, if only about 80% of the styrene repeat units of polystyrene are sulfonated, the resulting poly(styrenesulfonic acid) has an average charge per repeat unit of about −0.8.

Examples of a negatively-charged synthetic polyelectrolyte include polyelectrolytes comprising a sulfonate group ($-SO_3^-$), such as poly(styrenesulfonic acid) (PSS), poly(2-acrylamido-2-methyl-1-propane sulfonic acid) (PAMPS), sulfonated poly(ether ether ketone) (SPEEK), poly(ethylenesulfonic acid), poly(methacryloxyethylsulfonic acid), their salts, and copolymers thereof; polycarboxylates such as poly(acrylic acid) (PAA) and poly(methacrylic acid), polyphosphates, and polyphosphonates. Polylactic acid, polyglycolic acid and their copolymers are FDA approved but they are known to be biodegradable.

Examples of a positively-charged synthetic polyelectrolyte include polyelectrolytes comprising a quaternary ammonium group, such as poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), including poly(N-methyl-2-vinylpyridinium) (PM2VP), other poly(N-alkylvinylpyridines), and copolymers thereof; protonated polyamines such as poly(allylaminehydrochloride) (PAH) and polyethyleneimine (PEI); polysulfoniums, and polyphosphoniums.

Exemplary polyelectrolyte repeat units, both positively charged and negatively charged, are shown in Table I.

TABLE I

Polyelectrolyte Repeat Units

| Repeat Unit Name | Repeat Unit Structure |
| --- | --- |
| diallyldimethylammonium (PDADMA) | |
| styrenesulfonic acid (PSS) | |
| N-methyl-2-vinyl pyridinium (PM2VP) | |
| N-methyl-4-vinylpyridinium (PM4VP) | |
| N-octyl-4-vinylpyridinium (PNO4VP) | |
| N-methyl-2-vinyl pyridinium-co-ethyleneoxide (PM2VP-co-PEO) | |
| acrylic acid (PAA) | |
| allylamine (PAH) | |
| ethyleneimine (PEI) | |

Further examples of oppositely-charged polyelectrolytes include charged biomacromolecules, which are naturally occurring polyelectrolytes, or synthetically modified charged derivatives of naturally occurring biomacromolecules, such as modified celluloses, chitosan, or guar gum. A positively-charged biomacromolecule comprises a protonated sub-unit (e.g., protonated amines). Some negatively charged biomacromolecules comprise a deprotonated sub-unit (e.g., deprotonated carboxylates or phosphates). Examples of biomacromolecules which may be charged for use in accordance with the present invention include proteins, polypeptides, enzymes, DNA, RNA, glycosaminoglycans (e.g. heparin, hyaluronate, chondroitin sulfate), alginic acid, chitosan, chitosan sulfate, cellulose sulfate, polysaccharides, dextran sulfate, carrageenin, sulfonated lignin, and carboxymethylcellulose.

Natural, or biological, polyelectrolytes typically exhibit greater complexity in their structure than synthetic polyelectrolytes. For example, proteins may comprise any combination of about 2 dozen amino acid building blocks. Polymeric nucleic acids such as DNA and RNA may also comprise many different monomer repeat units. The sign and magnitude of the charge on proteins depends on the solution pH, as the charge on proteins is carried by weak acids, such as carboxylates (—COOH), or weak bases, such as primary, secondary, and tertiary amines Thus, at high pH (basic conditions) amines are deprotonated and uncharged, and carboxylate groups are deprotonated and charged. At low pH (acidic conditions) amines are protonated and charged, and carboxylate groups are protonated and uncharged. For proteins, there is a pH at which there are equal numbers of positive and negative charges on the biomolecule, and it is thus electrically neutral. This is termed the isoelectric point, or pI. At pH above the isoelectric point, the protein has a net negative charge and at pH below pI, proteins bear a net positive charge. Proteins that tend to have a preponderance of positive charge at physiological pH, characterized by a high pI, are often termed "basic" proteins, and proteins with a low pI are called "acidic" proteins.

The molecular weight (number average) of synthetic polyelectrolyte molecules is typically about 1,000 to about 5,000,000 grams/mole, preferably about 10,000 to about 1,000,000 grams/mole. The molecular weight of naturally occurring polyelectrolyte molecules (i.e., biomacromolecules), however, can reach as high as 10,000,000 grams/mole. The polyelectrolyte solution typically comprises about 0.01% to about 50% by weight of a polyelectrolyte, and preferably about 1% to about 20% by weight.

Many of the foregoing polymers/polyelectrolytes, such as PDADMA and PEI, exhibit some degree of branching. Branching may occur at random or at regular locations along the backbone of the polymer. Branching may also occur from a central point and in such a case the polymer is referred to as a "star" polymer, if generally linear strands of polymer emanate from the central point. If, however, branching continues to propagate away from the central point, the polymer is referred to as a "dendritic" polymer. Branched polyelectrolytes, including star polymers, comb polymers, graft polymers, and dendritic polymers, are also suitable for purposes of this invention. Block polyelectrolytes, wherein a macromolecule comprises at least one block of charged repeat units, are also suitable. The number of blocks may be 2 to 5. Preferably, the number of blocks is 2 or 3. If the number of blocks is 3 the block arrangement is preferably ABA.

Many of the foregoing polyelectrolytes have a very low toxicity. In fact, poly(diallyldimethylammonium chloride), poly(2-acrylamido-2-methyl-1-propane sulfonic acid) and their copolymers are used in the personal care industry, e.g., in shampoos. Also, because the polyelectrolytes used in the method of the present invention are synthetic or synthetically modified natural polymers, their properties (e.g., charge density, viscosity, water solubility, and response to pH) may be tailored by adjusting their composition.

By definition, a polyelectrolyte solution comprises a solvent. An appropriate solvent is one in which the selected polyelectrolyte is soluble. Thus, the appropriate solvent is dependent upon whether the polyelectrolyte is considered to be hydrophobic or hydrophilic. A hydrophobic polymer displays less favorable interaction energy with water than a hydrophilic polymer. While a hydrophilic polymer is water soluble, a hydrophobic polymer may only be sparingly soluble in water, or, more likely, insoluble in water. Likewise, a hydrophobic polymer is more likely to be soluble in organic solvents than a hydrophilic polymer. In general, the higher the carbon to charge ratio of the polymer, the more hydrophobic it tends to be. For example, polyvinyl pyridine alkylated with a methyl group (PNMVP) is considered to be hydrophilic, whereas polyvinyl pyridine alkylated with an octyl group (PNOVP) is considered to be hydrophobic. Thus, water is preferably used as the solvent for hydrophilic polyelectrolytes and organic solvents such as ethanol, methanol, dimethylformamide, acetonitrile, carbon tetrachloride, and methylene chloride are preferably used for hydrophobic polyelectrolytes. Even if polyelectrolyte complexes are prepared by mixing organic-soluble and water-soluble polymers, the complex is preferably rinsed to remove organic solvents before it is reshaped according to the method described herein. Some organic solvents are hard to remove even with extensive rinsing. Therefore, the preferred solvent for polyelectrolyte complexation is water.

Examples of polyelectrolytes that are soluble in water include poly(styrenesulfonic acid), poly(2-acrylamido-2-methyl-1-propane sulfonic acid), sulfonated lignin, poly(ethylenesulfonic acid), poly(methacryloxyethylsulfonic acid), poly(acrylic acids), poly(methacrylic acids), their salts, and copolymers thereof; as well as poly(diallyldimethylammonium chloride), poly(vinylbenzyltrimethylammonium), ionenes, poly(acryloxyethyltrimethyl ammonium chloride), poly(methacryloxy(2-hydroxy)propyltrimethyl ammonium chloride), and copolymers thereof; and polyelectrolytes comprising a pyridinium group, such as, poly(N-methylvinylpyridium), and protonated polyamines, such as, poly(allylamine hydrochloride) and poly(ethyleneimine).

Examples of polyelectrolytes that are soluble in non-aqueous solvents, such as ethanol, methanol, dimethylformamide, acetonitrile, carbon tetrachloride, and methylene chloride include poly(N-alkylvinylpyridines), and copolymers thereof in which the alkyl group is longer than about 4 carbon atoms. Other examples of polyelectrolytes soluble in organic solvents include poly(styrenesulfonic acid), poly(diallyldimethylammonium chloride), poly(N-methylvinylpyridinium) and poly(ethyleneimine) where the small polymer counterion, such as chloride or bromide, has been replaced by a large hydrophobic counterion such as tetrabutyl ammonium, tetraethyl ammonium, iodine, hexafluorophosphate, tetrafluoroborate, or trifluoromethane sulfonate.

The charged polyelectrolyte may be a synthetic copolymer comprising pH sensitive repeat units, pH insensitive repeat units, or a combination of pH sensitive repeat units and pH insensitive repeat units. pH insensitive repeat units maintain the same charge over the working pH range of use. The rationale behind such a mixture of pH sensitive groups and pH insensitive groups on the same molecule is that the pH insensitive groups interact with other, oppositely-charged pH insensitive groups on other polymers, holding the multilayer together despite the state of ionization of the pH sensitive groups.

For example, poly(acrylic acids) and derivatives begin to take on a negative charge within the range of about pH 4 to about 6 and are negatively charged at higher pH levels. Below this transition pH range, however, poly(acrylic acids) are protonated (i.e., uncharged). Similarly, polyamines and derivative thereof take on a positive charge if the pH of the solution is below their $pK_a$. As such, and in accordance with the present invention, the pH of a polyelectrolyte solution may be adjusted by the addition of an acid and/or base in order to attain, maintain, and/or adjust the electrical charge of a polyelectrolyte at the surface of, or within, a polyelectrolyte complex.

The state of ionization, or average charge per repeat unit, for polyelectrolytes bearing pH sensitive groups depends on the pH of the solution. For example, a polyelectrolyte comprising 100 pH insensitive positively charged units, such as DADMA, and 30 pH sensitive negatively charged units, such as acrylic acid, AA, will have a net charge of +100 at low pH (where the AA units are neutral) and an average of +100/130 charge per repeat unit; and a net charge of +70 at high pH (where 30 ionized AA units cancel out 30 of the positive charges) and an average of +70/130 charge per repeat unit. The different monomer units may be arranged randomly along the polymer chain ("random" copolymer) or they may exist as blocks ("block" copolymer). The average charge per repeat unit is also known as the "charge density."

pH sensitive polyelectrolyte complexes comprise pH sensitive polymeric repeat units, selected for example, from moieties containing carboxylates, pyridines, imidazoles, piperidines, phosphonates, primary, secondary and tertiary amines, and combinations thereof. Therefore, preferred polyelectrolytes used in accordance with this invention include copolymers comprising carboxylic acids, such as poly(acrylic acids), poly(methacrylic acids), poly(carboxylic acids), and copolymers thereof. Additional preferred polyelectrolytes comprise protonatable nitrogens, such as poly(pyridines), poly(imidazoles), poly(piperidines), and poly(amines) bearing primary, secondary or tertiary amine groups, such as poly(allylamine).

To avoid disruption and possible decomposition of the polyelectrolyte complex, polyelectrolytes comprising pH sensitive repeat units additionally comprise pH insensitive charged functionality on the same molecule. In one embodiment, the pH insensitive repeat unit is a positively charged repeat unit selected from the group consisting of repeat units containing a quaternary nitrogen atom, a sulfonium ($S^+$) atom, or a phosphonium atom. Thus, for example, the quaternary nitrogen may be part of a quaternary ammonium moiety ($—N^+R_aR_bR_c$ wherein $R_a$, $R_b$, and $R_c$ are independently alkyl, aryl, or mixed alkyl and aryl), a pyridinium moiety, a bipyridinium moiety or an imidazolium moiety, the sulfonium atom may be part of a sulfonium moiety ($—S^+R_dR_e$ wherein $R_d$ and $R_e$ are independently alkyl, aryl, or mixed alkyl and aryl) and the phosphonium atom may be part of a phosphonium moiety ($—P^+R_fR_gR_h$ wherein $R_f$, $R_g$, and $R_h$ are independently alkyl, aryl, or mixed alkyl and aryl). In another embodiment, the pH insensitive repeat unit is a negatively charged repeat unit selected from the group consisting of repeat units containing a sulfonate ($—SO_3^-$), a phosphate ($—OPO_3^-$), or a sulfate ($—SO_4^-$).

Exemplary negatively charged pH insensitive charged repeat units include styrenesulfonic acid, 2-acrylamido-2-methyl-1-propane sulfonic acid, sulfonated lignin, ethylenesulfonic acid, methacryloxyethylsulfonic acid, sulfonated ether ether ketone, phosphate. Preferred pH insensitive negatively charged polyelectrolytes include polyelectrolytes comprising a sulfonate group ($—SO_3^-$), such as poly(styrenesulfonic acid) (PSS), poly(2-acrylamido-2-methyl-1-propane sulfonic acid) (PAMPS), sulfonated poly(ether ether ketone) (SPEEK), sulfonated lignin, poly(ethylenesulfonic acid), poly(methacryloxyethylsulfonic acid), their salts, and copolymers thereof.

Exemplary positively charged pH insensitive repeat units include diallyldimethylammonium, vinylbenzyltrimethylammonium, ionenes, acryloxyethyltrimethyl ammonium chloride, methacryloxy(2-hydroxy)propyltrimethyl ammonium, N-methylvinylpyridinium, other N-alkylvinyl pyridiniums, a N-aryl vinyl pyridinium, alkyl- or aryl imidazolium, sulfonium, or phosphonium. Preferred pH insensitive positively-charged polyelectrolytes comprising a quaternary ammonium group, such as poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), other poly(N-alkylvinylpyridines), and copolymers thereof.

For illustrative purposes, certain of the pH insensitive positively-charged moieties are illustrated below:

Pyridinium having the structure:

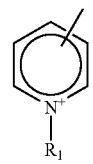

wherein $R_1$ is optionally substituted alkyl, aryl, alkaryl, alkoxy or heterocyclo. Preferably, $R_1$ is alkyl or aryl, and still more preferably $R_1$ is methyl;

Imidazolium having the structure:

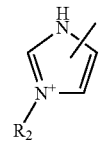

wherein $R_2$ is optionally substituted alkyl, aryl, alkaryl, alkoxy or heterocyclo. Preferably, $R_2$ is alkyl or aryl, and still more preferably $R_2$ is methyl;

Bipyridinium having the structure:

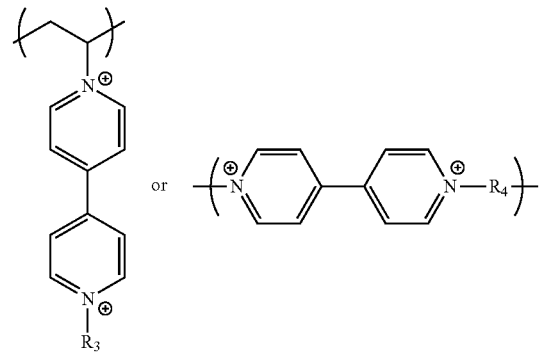

wherein $R_3$ and $R_4$ are optionally substituted alkyl, aryl, alkaryl, alkoxy or heterocyclo. Preferably, $R_3$ and $R_4$ are alkyl or aryl, and still more preferably $R_3$ is methyl.

The pH insensitive polyelectrolyte may comprise a repeat unit that contains protonatable functionality, wherein the functionality has a pKa outside the range of experimental use. For example, poly(ethyleneimine) has protonatable amine functionality with pKa in the range 8-10, and is thus fully charged (protonated) if the experimental conditions do not surpass a pH of about 7.

Preferably, the pH insensitive groups constitute about 10 mol % to about 100 mol % of the repeat units of the polyelectrolyte, more preferably from about 20 mol % to about 80 mol %. Preferably, the pH sensitive groups constitute about 30 mol % to about 70 mol % of the repeat units of the polyelectrolyte.

Optionally, the polyelectrolytes comprise an uncharged repeat unit that is not pH sensitive in the operating pH range, for example, about pH 3 to about pH 9. Said uncharged repeat unit is preferably hydrophilic. Preferred uncharged hydrophilic repeat units are acrylamide, vinyl pyrrolidone, ethylene oxide, and vinyl caprolactam. The structures of these uncharged repeat units are shown in Table II.

Some polymer repeat units exhibit a lower critical solution temperature (LCST). These units are preferred when additional temperature sensitivity is required from the complex. For example, Jaber and Schlenoff (Macromolecules, vol 38, p 1300 (2005)) disclose nonporous polyelectrolyte complex films comprising N-isopropylacrylamide units which become reversibly less hydrated and less permeable to small molecules at temperatures greater than about 35° C. In a preferred mode of use, the solid phase of the microporous article comprises polyelectrolyte complex further comprising temperature sensitive repeat units such as N-isopropylacrylamide and propylene oxide. Such a composition renders the solid phase of the article less permeable to small molecules at higher temperatures over a given temperature range.

disposal. It is an object of this invention to show how surfaces may be selected to encourage or discourage the adsorption of proteins to microporous polyelectrolyte complexes when they are used in vivo. Protein adsorption may be discouraged by copolymerizing with vinyl repeat units having hydrophilic groups, vinyl repeat units having zwitterionic groups, and hydrophilic repeat units.

Polyelectrolyte complexes comprising zwitterions useful for preventing protein and/or cell adhesion have been described in U.S. Pub No. 2005/0287111. It has been found that polymers comprising zwitterionic functional groups alone do not form polyelectrolyte complexes if they are employed under conditions that maintain their zwitterionic character. This is because the charges on zwitterionic groups do not exhibit intermolecular interactions. Therefore, preferred polymers comprising zwitterionic groups also comprise additional groups capable of intermolecular interactions, such as hydrogen bonding or ion pairing. More preferably, polyelectrolytes comprising zwitterionic groups also comprise charged groups that are not zwitterionic. Zwitterionic groups are present on polyelectrolytes as blocks or randomly dispersed throughout the polymer chain. Preferably, polyelectrolytes comprise between about 1% and about 90% zwitterions units, and more preferably said polyelectrolyte comprises between about 10% and about 70% zwitterionic units. Preferred compositions of polyelectrolytes comprising zwitterionic repeat units also comprise between about 10% and about 90% non-zwitterionic charged repeat units. Preferred zwitterionic repeat units are poly(3-[2-(acrylamido)-ethyldimethyl ammonio]propane sulfonate) (PAEDAPS) and poly(N-propane sulfonate-2-vinyl pyridine) (P2PSVP). The structures of these zwitterions are shown in Table III.

TABLE II

Neutral Repeat Units

| Repeat Unit Name | Repeat Unit Structure |
|---|---|
| Acrylamide | [structure] |
| Vinylpyrrolidone | [structure] |
| Ethylene oxide | [structure] |
| Vinylcaprolactam | [structure] |

TABLE III

Zwitterionic Repeat Units

| Name | Structure |
|---|---|
| 3-[2-(acrylamido)-ethyldimethyl ammonio] propane sulfonate (AEDAPS) | [structure] |
| N-propane sulfonate-2-vinyl pyridine (2PSVP) | [structure] |

Protein adsorption is driven by the net influence of various interdependent interactions between and within surfaces and biopolymer. Possible protein-polyelectrolyte interactions can arise from 1) van der Waals forces 2) dipolar or hydrogen bonds 3) electrostatic forces 4) hydrophobic effects. Given the apparent range and strength of electrostatic forces, it is generally accepted that the surface charge plays a major role in adsorption. However, proteins are remarkably tenacious adsorbers, due to the other interaction mechanisms at their It has been disclosed by Graul and Schlenoff (Anal. Chem., 71, 4007 (1999)) that polyelectrolyte films prepared by the multilayering method are able to control the adsorption of protein. It is also generally known by those skilled in the art that hydrophilic units, such as ethylene oxide (or ethylene glycol), are effective in reducing the overall propensity of biological macromolecules, or biomacromolecules, to adsorb to surfaces (see Harris, *Poly(ethylene glycol) Chemistry: Biotechnical and Biomedical Applications*, Plenum Press, New York, 1992). Yang and Sundberg (U.S. Pat. No. 6,660,367) disclose materials comprising ethylene glycol units that are effective at resisting the adsorption of hydrophilic proteins in microfluidic devices. The ethylene oxide (or ethylene glycol) repeat units are preferably present as blocks within a block copolymer. Preferably, the block copolymer also comprises blocks of charged repeat units, allowing the material to be incorporated into a polyelectrolyte complex. Sufficient ethylene oxide repeat units are required to promote resistance to protein adsorption, but too many ethylene oxide units do not allow polyelectrolyte complexes to associate. Therefore, the preferred ratio of charged to neutral blocks in a polyelectrolyte complex from 10:1 to 1:4, and a more preferred ratio is 5:1 to 1:2.

In some applications, the microporous article comprises polyelectrolyte that renders the article biocompatible. Preferred polyelectrolytes for biocompatibility comprise fluorinated polymers, preferably fluorinated polyelectrolytes. See, for example, U.S. Pub. No. 2005/0287111, the entire contents of which are hereby incorporated in their entirety. Fluorinated polyelectrolytes are preferably copolymers, or copolyelectrolytes, comprising fluorinated and non-fluorinated repeat units. Said repeat units may be disposed in a random or block fashion on the backbone of said copolyelectrolytes. Preferred fluorinated copolyelectrolytes comprise charged non-fluorinated with noncharged fluorinated repeat units, or charged fluorinated with noncharged nonfluorinated repeat units. Other preferred fluorinated polyelectrolytes comprise charged fluorinated repeat units with charged nonfluorinated repeat units. Fluorinated copolyelectrolytes are preferably made by post-polymerization reactions on polymers, such as alkylation, or by polymerization of fluorinated monomers or mixtures of fluorinated monomers. Mole percentages of fluorinated repeat units on fluorinated copolyelectrolytes are preferably from 10% to 95%, and more preferably from 20% to 95%.

For illustrative purposes, certain fluorinated moieties are shown as vinyl repeat units:

Vinyl Polymer Repeat Unit

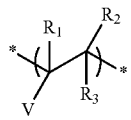

wherein $R_1$, $R_2$, and $R_3$ are each independently —$(CH_2)_m$H or —$(CH_xF_{2-x})_n$F and m and n are independently 0 to 12, x is 0, 1, or 2 and V is a group selected from among the following:

fluorinated hydrocarbons having the structure:
—$(CH_2)_p(CF_2)_qF$, —$(CH_2)_p(CF_2)_qCOOH$, —$(CH_2)_p(CF_2)_qOPO_3^-$, —$(CH_2)_p(CF_2)_qSO_3^-$, —$(CH_2)_p(CF_2)_qOSO_3^-$, —$O(CH_2)_p(CF_2)_qF$, —$O(CH_2)_p(CF_2)_qSO_3^-$, and
wherein p is 0 to 6 and q is 1 to 21;

fluorinated amides having the structure:

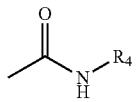

wherein $R_4$ is —$(CH_2)_p(CF_2)_qF$, —$(CH_2)_p(CF_2)_qCOOH$, —$(CH_2)_p(CF_2)_qOPO_3^-$, —$(CH_2)_p(CF_2)_qSO_3^-$, —$(CH_2)_p(CF_2)_qOSO_3^-$, and
wherein p is 0 to 6 and q is 1 to 21;

fluorinated esters having the structure:

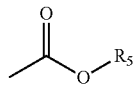

wherein $R_5$ is —$(CH_2)_p(CF_2)_qF$, —$(CH_2)_p(CF_2)_qCOOH$, —$(CH_2)_p(CF_2)_qOPO_3^-$, —$(CH_2)_p(CF_2)_qSO_3^-$, —$(CH_2)_p(CF_2)_qOSO_3^-$, and
wherein p is 0 to 6 and q is 1 to 21;

fluorinated phenyl groups having the structure:

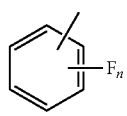

wherein n is 2 to 5; or

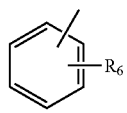

wherein $R_6$ is —$(CH_2)_p(CF_2)_qF$ or —$O(CH_2)_p(CF_2)_qF$ and wherein p is 0 to 6 and q is 1 to 21;

fluorinated pyridiniums having the structure:

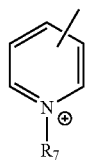

wherein $R_7$ is —$(CH_2)_p(CF_2)_qF$ and wherein p is 0 to 6 and q is 1 to 21;

fluorinated imidazoliums having the structure:

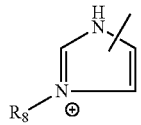

wherein $R_8$ is —$(CH_2)_p(CF_2)_qF$ and wherein p is 0 to 6 and q is 1 to 21;

fluorinated quaternary nitrogens having the structure:

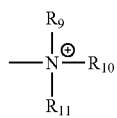

wherein $R_9$, $R_{10}$, and $R_{11}$ are each independently —$(CH_2)_p(CF_2)_qF$ and wherein p is 0 to 6 and q is 1 to 21 or -arylF$_z$ wherein z is 2 to 8;

fluorinated sulfoniums having the structure:

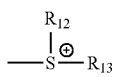

wherein $R_{12}$ and $R_{13}$ are each independently —$(CH_2)_p(CF_2)_qF$ wherein p is 0 to 6 and q is 1 to 21 or -aryl$F_z$ wherein z is 2 to 8; and fluorinated phosphoniums having the structure:

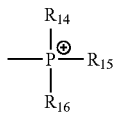

wherein $R_{14}$, $R_{15}$, and $R_{16}$ are each independently —$(CH_2)_p(CF_2)_qF$ wherein p is 0 to 6 and q is 1 to 21 or -aryl$F_z$ where z=2 to 8.

For illustrative purposes, certain of these moieties are shown as allyl repeat units (e.g., PDADMA):

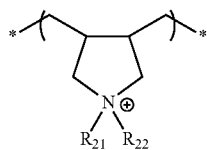

wherein $R_{21}$ and $R_{22}$ are —$(CH_2)_p(CF_2)_qF$, wherein p and q are independently selected for $R_{21}$ and $R_{22}$, and p is 0 to 6 and q is 1 to 21.

Table IV shows the structures of fluorinated polyelectrolytes that may be present in the polyelectrolyte complex articles of the present invention.

TABLE IV

| Fluorinated Polyelectrolyte Repeat Units | |
|---|---|
| Name | Structure |
| 4-vinyl-trideca-fluoro-octyl pyridinium iodide-co-4-vinyl pyridine (PFPVP) | (structure shown) Where M is a mole fraction typically from about 0.1 to about 1.0, preferably from about 0.3 to about 0.8 |
| NAFION® | (structure shown) Where X, Y, and X denote molar proportions; X may be from about 6 to about 10 parts, Y may be about 1 part and Z may be from about 1 to about 3 parts |

In one preferred embodiment, a small amount of chemical crosslinking is introduced into the polyelectrolyte complex for stability. Chemical crosslinking is preferably accomplished by including difunctional monomers in the polyelectrolytes comprising the complex. For example, a divinyl repeat unit added to the polymerization reaction will be incorporated into two polyelectrolyte chains, giving a crosslink at the connection point. Alternatively, an article may be treated with a difunctional crosslinking agent, such as $XCH_2$-ϕ-$CH_2X$, where X is a halogen (Cl, Br, or I) and ϕ is a phenyl group. The phenyl group may be replaced by another aromatic or aliphatic moiety, and easily-displaceable groups, such as toluene sulfonate, may replace the halogen. A preferred crosslinking agent is a dihalogenated compound, such as an aromatic or aliphatic dibromide, which is able to alkylate residual unalkylated units on two adjoining polyelectrolyte chains. Crosslinked materials are harder to deform. Since during the preferred method of use the microporous article is deformed the level of chemical crosslinking, prior to deforming, should be kept low, preferably less than 2%. If crosslinking is desired, it is preferably introduced after the deformation step.

Another preferred method of chemical crosslinking a polyelectrolyte complex is heat treatment. For example, Dai et al. (*Langmuir* 17, 931 (2001)) disclose a method of forming amide crosslinks by heating a polyelectrolyte multilayer comprising amine and carboxylic acid groups. Yet another preferred method of introducing crosslinking, disclosed by Kozlovskaya et al. (Macromolecules, 36, 8590 (2003)) is by the addition of a carbodiimide, which activates chemical crosslinking. The level of chemical crosslinking is preferably 0.01% to 50%, and more preferably 0.1% to 10%.

Another method of chemical crosslinking of a microporous polyelectrolyte complex is by photocrosslinking. Photocrosslinking may be achieved by the light-induced decomposition or transformation of functional groups that form part of the polymer molecules. See, for example, Strehmel, Veronika, "Epoxies: Structures, Photoinduced Cross-linking, Network Properties, and Applications"; Handbook of Photochemistry and Photobiology (2003), 2, 1-110. See also Allen, Norman S., "Polymer photochemistry", Photochemistry (2004), 35, 206-271; Timpe, Hans-Joachim "Polymer photochemistry and photocrosslinking" Desk Reference of Functional Polymers (1997), 273-291, and Smets, G., "Photocrosslinkable polymers", Journal of Macromolecular Science, Chemistry (1984), A21 (13-14), 1695-703. Alternatively, photocrosslinking of a polyelectrolyte complex may be accomplished by infusing the formed polyelectrolyte complex with a small photoactive crosslinker molecule, then exposing the polyelectrolyte complex to light.

In some embodiments, the polyelectrolyte complex comprises further physical crosslinks created by hydrogen bonding. Hydrogen bonding is weaker than chemical bonding and occurs between a hydrogen bond donor and a hydrogen bond acceptor. Hydrogen bonds are minimally impacted by the presence of salt and thus the level of physical crosslinking due to hydrogen bonding remains substantially the same as the salt concentration is varied. Accordingly, the polyelectrolyte complex further comprises polymer repeat units capable of hydrogen bonding. Examples of hydrogen bond donor/acceptor pairs are presented in U.S. Pat. Nos. 6,740,409 and 7,470,449 as well as U.S. Pat. Publication 2005/0163714.

Salt Content

In one embodiment, the microporous polyelectrolyte complex of the present invention may be shaped in a manner that incorporates a significant salt ionic concentration within the bulk of the microporous article. The salt ionic concentration is preferably achieved by shaping microporous articles in contact with solutions comprising salt ions. Stated differently, the polyelectrolyte complex is doped with salt ions to increase the ionic strength and decrease the extent of ionic crosslinking of the polyelectrolyte complex. The extent of doping and the identity of the salt ions may be varied precisely to advantageously control the forming characteristics of the polyelectrolyte complex. Sources of salt ions for doping include the polyelectrolyte material, and from salt. Salts include soluble, ionic compounds that dissociate in solution to stable ions (e.g., sodium chloride). A salt may comprise organic ions, inorganic ions, or a combination of organic and inorganic ions. For physiological applications, ions selected to control mechanical properties are preferably of minimal toxicity. Anions and/or cations with charge greater than one are preferred for inducing greater doping at lower concentration.

A wide variety of salt ions may be added to the microporous polyelectrolyte complex to induce doped shapeable materials in the method of the present invention. In general, the salt may comprise any cation selected from among the alkali metal cations, alkaline earth metal cations, transition metal cations, semi-metallic cations, and organic cations such as amines. The salt(s) may comprise a mixture of two or more of any of these cations. Among the alkali metal cations, lithium, sodium, potassium, and rubidium may be incorporated into the microporous article, with sodium and potassium being particularly preferred. In certain physiological applications, the choice of alkali metal cations may be limited to sodium or potassium ions. Among the alkaline earth metal cations, magnesium, calcium, strontium, and barium may be incorporated into the microporous article. Calcium and magnesium cations are particularly preferred, and for physiological applications, the choice of alkaline earth metal cations may be limited to calcium and magnesium. A wide variety of transition metals may be incorporated into the microporous article including scandium, yttrium, titanium zirconium, vanadium, niobium, chromium, molybdenum, manganese, iron, ruthenium, cobalt, rhodium, nickel, palladium, platinum, copper, silver, gold, and zinc. In certain physiological applications, the choice of transition metal cations may be limited to zinc, silver, iron, and copper. Other metal cations that may be incorporated into the microporous articles include aluminum, indium, tin, lead, and bismuth. Organic cations that may be included include ammonium, primary, secondary, tertiary, and quaternary amines comprising alkyl groups having from one to four carbon atoms. Primary amines, secondary amines, and tertiary amines are protonated to achieve positive charge and are thus pH sensitive. Exemplary primary amines, secondary amines, and tertiary amines are protonated forms of methylamine, dimethylamine, trimethyl amine, ethylamine, diethylamine, and triethylamine among others. Quaternary amines are pH insensitive groups. Exemplary quaternary amines include tetramethylammonium, tetraethylammonium, tetrapropylammonium, among others. In one embodiment, the amine is a linear polyamine such as ethylene diamine, diethylene triamine, dipropylene triamine, triethylene tetraamine, tripropylene tetraamine, tetraethylene pentaamine, tetrapropylene pentaamine, spermine, or spermidine.

The anion may be selected from among halide anions, oxoanions, and organic anions. A combination of anions may be incorporated into the microporous article. Halide ions that may be incorporated into the microporous article include fluoride, chloride, bromide, and iodide. Advantageously, any of these halides may be incorporated into microporous articles for use in physiological applications. In one preferred embodiment, the halide anion is chloride ion. In another preferred embodiment, the halide anion is chloride ion with a relatively low concentration of fluoride ion. Incorporation of a low concentration of fluoride ion is advantageous when the reshaped article is used in or near bone, such as in dental implants or in the intervertebral space. Oxoanions that may be incorporated into the microporous article include sulfonate, sulfate, sulfite, phosphate, phosphite, phosphonate, pyrophosphate, hypochlorite, chlorite, chlorate, perchlorate, iodate, periodate, bromate, borate, carbonate, nitrate, nitrate, aluminate, and manganate, among others. Organic anions that may be incorporated into the microporous article include carboxylates, such as citrate, lactate, acetate, benzoate, formate, malate, malonate, fumarate, oxalate, propionate, butyrate, tartrate, and valerate, phthalate, among others. Hydrophobic anions, such as those with a high hydrocarbon to charge ratio, are preferred for enhancing doping. Preferred organic anions for physiological applications include citrate and lactate. Organic solvent is optionally added to the aqueous salt solution during doping and during forming as long as the doping level remains within the preferred range during the forming step when force is applied.

In view of the above cations and anions, a wide variety of salts may be incorporated into the microporous articles of the present invention. Preferably, the salts are soluble in aqueous solution at a concentration at least sufficient to incorporate ions into the microporous article to an extent sufficient to achieve the desired doping level. In some embodiments, however, a relatively insoluble salt may be incorporated to impart some other desired characteristic, for example, biocompatibility. In these embodiments, the insoluble salt may be present in the polyelectrolyte solutions in a relatively low concentration and may be combined with another salt having high solubility. For example, calcium citrate has relatively low solubility (about 0.01 M in 0.1 M HCl). In certain applications, it may be desirable to include calcium citrate, but its limited solubility hinders its ability to substantially affect the article's elastic doping level. Therefore, the polyelectrolyte solution may further comprise a highly soluble salt, such as sodium chloride, for example, that will become incorporated in a high enough concentration to achieve the desired doping level.

Particularly preferred salts include chloride salts, citrate salts, and phosphate salts. Preferred chloride salts include sodium chloride, potassium chloride, magnesium chloride, calcium chloride, and aluminum chloride. Preferred citrate salts include trisodium citrate, disodium hydrogencitrate, sodium dihydrogencitrate, tripotassium citrate, dipotassium hydrogencitrate, potassium dihydrogencitrate, magnesium citrate, and calcium citrate. Preferred phosphate salts include trisodium phosphate, disodium hydrogen phosphate, sodium dihydrogen phosphate, tripotassium phosphate, dipotassium hydrogen phosphate, potassium dihydrogen phosphate, disodium potassium phosphate, sodium dipotassium phosphate, sodium potassium hydrogen phosphate, calcium phosphate, and magnesium phosphate.

As stated above, doping of the microporous polyelectrolyte complex affects the elastic and dynamic mechanical properties of the article comprising the complex, such as, for example, the elastic and complex shear modulus. It has been observed that increasing the salt concentration decreases the article's $G^*$. Conversely, decreasing the salt concentration increases $G^*$, making the article harder and tougher. It has also been observed that incorporation of cations and anions having multiple valences (i.e., an absolute charge of two or greater) for a given concentration decreases elastic modulus and $G^*$ to a greater extent than does incorporation of singly charged cations and anions. For example, incorporating calcium chloride into the microporous polyelectrolyte complex by maintaining it in a solution having a calcium chloride concentration of 0.2 M decreases the article's elastic and shear moduli to a greater extent than does maintaining the article in the presence of solution comprising sodium chloride at a concentration of 0.2 M. The difference between contacting the polyelectrolyte complex with calcium chloride and sodium chloride is due to the greater doping level afforded by the same concentration of calcium chloride.

The process of doping is defined as the breaking of ion pair crosslinks by salt ions entering the polyelectrolyte complex. Salt ions electrically compensate the charges on the polyelectrolytes. In such a compensation, the salt ions are termed counterions. Salt ions residing in pores or paired with other salt ions or present as crystals are not considered to be doping the polyelectrolyte complex and do not contribute to the doping level. The level or density of doping is therefore inversely related to the crosslink density. Advantageously, the breaking of ion pair crosslinks by doping is reversible and under thermodynamic control. In contrast, chemical crosslinks are often irreversible.

Preferably, the doping level of polyelectrolyte complexes is created and maintained by contacting the complex with a solution comprising salt ions of a specific concentration. Equilibration of the polyelectrolyte complex in the salt solution in which the complex is immersed may be fairly rapid, with durations typically on the order of between about 1 minute and about 30 minutes per millimeter thickness of the microporous polyelectrolyte complex article.

The extent to which ion pair crosslinks have been replaced by salt counterions within the bulk of the microporous article comprising polyelectrolyte complex may be quantified in terms of a doping level or doping level ratio, determined by dividing the sum of the ionic charge provided by salt ions acting as counterions by the sum of charge provided by the polymer repeat units. This ratio may be expressed in terms of a doping level percentage by multiplying the doping level ratio by 100. The lowest doping level is 0.0 (0%) wherein all the positively charged polyelectrolyte repeat units are paired with all the negatively charged polyelectrolyte repeat units, which corresponds to the maximum level (100%) of ionic crosslinking. The highest doping level is 1.0 (100%), where all charged polyelectrolyte repeat units are paired with a salt ion. When the doping level is 1.0 the polyelectrolytes are dissociated: phase separation can occur between components; additives can phase separate, and solutions do not maintain their shape when formed. Therefore, a doping level of 1.0, wherein the polyelectrolyte complex is dissolved, or maintained in solution, as described in U.S. Pat. No. 3,546,142, is not preferred.

The doping level can be measured, for example by infrared absorption spectroscopy (see Farhat and Schlenoff, *Langmuir* 2001, 17, 1184; and Farhat and Schlenoff, *Journal of the American Chemical Society*, 2003, vol. 125, p. 4627.)

It has been shown quantitatively that the mechanical properties of articles comprising polyelectrolyte complex are influenced by the doping level. For example, Jaber and Schlenoff (e.g. see Journal of the American Chemical Society, 2006, vol. 128, p. 2940) analyzed the mechanical properties of articles comprising nonporous polyelectrolyte complexes using classical theories of rubber elasticity. The elastic modulus of articles comprising nonporous polyelectrolyte complexes decreased as they were doped with salt ions. In the doping level range studied, which was about 0 to about 0.4, the articles were elastically deformed, meaning that they regained their original shape when the deforming force, up to a percent strain of 2%, was removed. The preferred doping level for shaping a polyelectrolyte complex article in the method of the present invention is critically important. In order to shape a polyelectrolyte complex article into a persistent shape the doping level must be sufficiently high. In the method of the present invention it has been discovered that a doping level of at least 0.5 is required for forming a polyelectrolyte complex article into a persistent shape. Preferably, the doping level is between 0.6 and 0.990 and more preferably it is between 0.7 and 0.990. Stated in terms of a percentage, the doping level is preferably between about 60% and about 99.0%, more preferably between about 70% and about 99.0%. A doping level greater than 0.990 is to be avoided. To illustrate a doping level ratio calculation, suppose that a simple polyelectrolyte complex comprises a blend of one positively charged polyelectrolyte having 100 positively charged repeat units paired with one negatively charged polyelectrolyte having 100 negatively charged repeat units. Such a polyelectrolyte complex therefore has a total charge provided by the charged repeat units of 200. The number of ionic crosslinks is 100. This polyelectrolyte complex may be doped with salt ions which become associated with the charged repeat units. For example, if 10 sodium ions are associated with 10 negatively charged repeat units and 10 chloride ions are associated with 10 positively charged repeat units, the sum of charges provided by the salt ions is 20, and 10 ionic crosslinks have been broken. The doping level ratio is calculated by dividing the sum of charges of the salt ions by the sum of charges from the repeat units, i.e., 20/200=0.1, or 10%, stated as a doping level percentage. By way of further example, if 5 calcium ions (2+) are associated with 10 negatively charged repeat units and 10 chloride ions are associated with 10 positively charged repeat units, the sum of charges provided by the salt ions is 20 (=5×2 for the calcium+10 for the chloride) and the doping level ratio is 20/200=0.1, or 10%, stated as a doping level percentage. To achieve these doping levels, the article comprising the polyelectrolyte is preferably maintained in contact with a solution of the doping salt in water. The salt concentration employed during preparation and compaction includes those ions liberated from the polyelectrolytes by complexation.

Crosslinked rubbery materials are normally not suitable for reshaping. Without being held to a particular theory, it is believed that, at the preferred doping levels, the timescale for breaking and reforming ion pair crosslinks is faster than the timescale for reorganizing the polymer molecules during the reshaping step. Thus, the crosslinking is dynamic enough to allow the material to adopt a new, persistent shape at the end of the preferred method.

Methods of Forming

The method of forming an article comprising a microporous polyelectrolyte complex of the present invention includes those described in International Application No. PCT/US2007/077146 published as WO 2008/027989 and U.S. Provisional Application Ser. No. 61/089,286. These methods include compacting a solution-precipitated polyelectrolyte complex by a centrifugal field, as described in the below examples. It was discovered, and heretofore never disclosed, that the compacted polyelectrolyte obtained as described in the Examples section was microporous with a total sample pore volume between 50 and 80%. In addition, it was discovered that these microporous complexes could be deformed to a much greater extent than nonporous complexes.

One method for preparing articles in the form of a film or other body of a polyelectrolyte complex is by the alternating layer-by-layer deposition method. The preferred concentration of polyelectrolytes in solutions used to deposit in this manner is in the range 0.01 weight % to 10 weight %, and preferably 0.1 weight % to 1 weight %. The polyelectrolyte complex may be prepared by alternately exposing a surface of a substrate to two or more solutions, each comprising a polyelectrolyte until a polyelectrolyte complex of a desired thickness, typically from about 100 nm to about 10,000 nm, is reached. These thicknesses may be typically be achieved by alternately layering between about two and about 1000 nominal layers of polyelectrolyte. At least one solution comprises a predominantly positively charged polyelectrolyte and at least one solution comprises a predominantly negatively charged polyelectrolyte. The alternating polyelectrolyte layering method, however, does not generally result in a layered morphology of the polymers with the film. Rather, the polymeric components interdiffuse and mix on a molecular level upon incorporation into the thin film. See Losche et al., *Macromolecules* 31, 8893 (1998). The complexed polyelectrolyte within the film has similar morphology as a polyelectrolyte complex formed by mixing solutions of positive and negative polyelectrolyte followed by ultracentrifugation in the presence of salt, as described in the present invention. These polyelectrolyte complex films rarely exceed 1 μm in thickness.

Thicker films may be prepared in accordance with one method of the present invention. In general, larger quantities of polyelectrolyte complex are typically prepared by combining separate solutions, each containing one of the polyelectrolytes. At least one solution comprises a predominantly positively-charged polyelectrolyte, and at least one solution comprises a predominantly negatively-charged polyelectrolyte. The solutions are combined in a manner that allows the positively-charged polyelectrolyte and the negatively-charged polyelectrolyte to intermix. Intermixing the respective polyelectrolytes causes the in situ formation of a polyelectrolyte complex comprising an intermolecular blend of the positively-charged polyelectrolyte and the negatively-charged polyelectrolyte. Preferably, at least one of the solutions comprises salt ions, such that salt ions also intermix with and become part of the polyelectrolyte complex. The resulting polyelectrolyte complex may simply be allowed to precipitate and settle to the bottom of the container. The supernatant is, in a preferred embodiment, separated to the extent possible from the polyelectrolyte complex. In addition, a substantially compacted article may be obtained by centrifugation at high rates, and particularly in the presence of salt. When a complex is processed thus, it turns from an opaque, gelatinous, diffuse material into a solid plug that it often optically transparent. The plug may be removed and cut into a preferred shape with a razor blade. Accordingly, compacting the polyelectrolyte complex precipitate formed by the intermixing method preferably occurs in a centrifuge capable of obtaining a high rotation rate and g-force to achieve the desired complex modulus, $E^*$ or $G^*$. Preferably, the centrifuge is powerful enough to compact the polyelectrolyte complex into a plug, adopting the contours of the centrifuge vessel. Preferably, said vessel is shaped to produce a compacted article of the preferred geometry. More preferably, compaction occurs in the presence of a salt, which appears to enhance the ability of the centrifuge to compact the polyelectrolyte complex. The optimum centrifuging time is a function of the rotor size, defined as the distance between the axis of rotation and the bottom of the centrifuge tube while in motion, the rotation rate, the centrifuging time, the salt concentration, the salt composition, the polyelectrolyte types, the temperature, and the solvent. If pH-dependent groups are present the centrifuge time for compaction also depends on the solution pH. The combination of rotor size and rotation rate is often combined into a single g-force quantity, where the rotational centrifuge force, RCF, in units of g, is given by $RCF=1.12\times10^{-5}rN^2$, where r is the radius (cm) of the rotor and N is the rotational speed (rpm).

Centrifugal compaction preferably occurs at speeds of rotation of greater than 10,000 rpm (at a rotor size between about 5 cm and about 30 cm and more preferably at greater than 20,000 rpm (at a rotor size between about 10 cm and about 20 cm). Stated in terms of g-force, centrifugal compaction preferably occurs at g-forces between about 10,000 g and about 1,000,000 g, such as between about 100,000 g and about 500,000 g.

Centrifuge times between about 1 and about 100 minutes, such as between about 1 and about 10 minutes, at g-forces within the range stated above is typically sufficient to achieve an article comprising microporous polyelectrolyte complex of sufficient density and elastic modulus. As the rotation rate increases the time needed for centrifuging decreases. Increasing the salt concentration decreases the centrifuge time required, sometimes substantially. In some embodiments, the salt concentration is adjusted to be great enough such that the centrifuge time remains below 10 minutes. As a rough guide illustrating the interdependence of required g-forces and salt concentrations for effective polyelectrolyte compaction, the product g[NaCl] should be greater than 10,000. For example, a g-force of at least 10,000 at 1 M NaCl may achieve the desired degree of compaction, whereas a g-force of at least 100,000 may be desired for compaction in the presence of 0.1 M NaCl. More hydrated polyelectrolyte complexes are easier to compact at a given salt concentration. As a rough guide, the formula for minimum g-force may be used: $g[NaCl](100-wt\% H_2O)>1\times10^7$. Where wt % $H_2O$ is the weight percent of water in the compacted complex.

Preferably, centrifugation is performed under conditions of ionic strength greater than 0.1 M. The ionic strength can range quite high, such as between about 0.1 M and about 5 M, preferably between about 0.1 M and about 2.0 M, more preferably between about 0.1 M and about 0.5 M. For example, complexes of PDADMA and PSS have been compacted in 2.5 M NaCl. In one embodiment, centrifugation may occur under conditions in which the sodium chloride concentration is between about 0.1 M and about 0.5 M, preferably between about 0.1 M and about 0.3 M in one embodiment. In another embodiment, centrifugation may occur under conditions in which the calcium chloride concentration is between about 0.1 M and about 0.4 M, preferably between about 0.15 M and about 0.3 M. These ionic strengths may be used to achieve compacted articles having G* at 10 Hz between about 1 kPa to about 300 MPa, more typically between about 10 kPa and about 100 MPa, even more typically between about 1 MPa and about 20 MPa, such as between about 1 MPa and about 10 MPa. Note that conditions employing higher ionic strength tend to yield a compacted article having G* near the higher end of the range of G* available for a particular polyelectrolyte complex article at a particular salt concentration. For example, centrifugation under conditions of 0.15 M sodium chloride concentration may yield a compacted article having an elastic modulus between about 1 and about 5 MPa. Preferably, the centrifugal compaction is performed at ionic strength higher than that at which the article is to be used. Preferably the ionic strength at which centrifugal compaction takes place is at least 20% greater than the ionic strength at which the article is used. The reason for the elevated ionic strength during centrifugation is that it facilitates the compaction process. For example, a polyelectrolyte complex may be compacted at 2.0 M salt concentration and then employed for use, for example as an in-vivo implanted medical device, at about 0.15 M electrolyte concentration (i.e. physiological). Excess salt, generated by the release of ions from the polyelectrolytes during precipitation, may be removed by washing or by dialysis.

A variety of salts, comprising monovalent or polyvalent cations and/or monovalent or polyvalent anions, may be used during the centrifugal compaction process. Preferably, the salt is NaCl. The salt may be present at the polyelectrolyte precipitation stage, or it may be present at the centrifugation stage. Preferably, a lower concentration of salt is present during precipitation, for example in the range of 0.1M, and a higher concentration is present during centrifugation, in the range of 1.0 M.

For applications requiring the insertion of an article comprising microporous polyelectrolyte complex in vivo, as a medical implant, it is not advantageous to use salt concentrations significantly higher than 0.15 M. This is because the osmotic pressure can shock surrounding tissue. However, it is advantageous to introduce the compacted object having a more flowable character and allow it to harden in vivo. For this purpose, it is preferable to employ a salt of calcium, aluminum or magnesium, preferably the chloride or citrate salt, in the centrifugal compaction process at physiological osmotic pressure, introduce the implant, then allow the implant ions to be replaced by physiological ions (i.e. mostly NaCl). Compacted complexes comprising substantially salts of calcium, aluminum or magnesium are more flowable than compacted complexes comprising NaCl at the same ionic strength.

If large changes in ionic strength between compaction and use are to be avoided, it is preferable to use a salt of calcium, aluminum, or magnesium preferably the citrate, chloride, or bromide during the compaction step. The use of salts other than sodium chloride is preferred when the ionic strength of NaCl required for good compaction is greater than about 2 M. As the concentration of salt increases the density of the solution increases. The higher solution density leads to less efficient centrifugal compaction. Therefore, the use of another salt, having improved compaction properties at lower concentration, is preferred. Examples of said alternative salts include those from calcium, aluminum or magnesium.

Optionally, heat may be applied to the solution during centrifugation. The purpose of the heat is to render the materials in the centrifugation process more flowable (lower viscosity). Preferably, the solution is heated between 30 and 90 degrees centigrade. Higher temperatures are possible, but the centrifuge container must be pressurized, as the solutions will boil at about 100 degrees centigrade.

Alternatively, the polyelectrolyte complexes may be compacted under pressure. In this method, individual polyelectrolytes in solution are mixed, preferably in the presence of salt. The gelatinous precipitate is then pressed against a filter membrane by hydrostatic pressure. The hydrostatic pressure may be between about 40 psi and about 10,000 psi, such as between about 100 psi and about 1000 psi, to achieve an article of desired modulus and density. The gelatinous polyelectrolyte complex suspension tends to plug up the pores of the filtration media, therefore, the filter medium preferably has pores of diameter less than 10 micrometer in diameter, more preferably of molecular dimensions of the solution polyelectrolytes. Pores of such small dimensions are obtained from porous anodized alumina or track-etched polymer membranes (e.g. "Nucleopore" which is track-etched polycarbonate). Examples of filters with pores smaller than polymer molecule dimensions include dialysis tubing (e.g. treated cellulose films) and membranes that are used in the art for reverse osmosis. The advantage of membranes with pores smaller than the molecular dimensions is that the polymer molecules do not plug the pores, while the disadvantage is that the filtration is slow. For precipitates that clog filters excessively, it is advantageous to employ filter media that have graded pore sizes, from larger to smaller pores going into the medium.

In yet another alternative, the polyelectrolyte complexes may be compacted under vacuum. In this method, individual polyelectrolytes in solution are mixed, preferably in the presence of salt. The gelatinous precipitate is then pressed against a filter membrane. A vacuum is then applied on the opposite side of the membrane, the vacuum being sufficient to pull water from the precipitate by suction. The gelatinous polyelectrolyte complex suspension may tend to plug up the pores of the filtration media, therefore, the filter medium preferably has pores of diameter less than 10 micrometer in diameter, more preferably of molecular dimensions of the solution polyelectrolytes.

Preparation of the article comprising microporous polyelectrolyte complexes according to the method of the present invention provides many advantages.

First of all, the method enables the preparation of articles having a wide range of transverse dimensions, such as, on the order of micrometers, millimeters, and even centimeters, wherein the transverse dimension is the distance between one surface of the article to another, opposing surface of the article. The transverse dimensions of the compacted articles may be a function of the desired gap distance between two abutting surfaces and the shape of the gap between the abutting surfaces, wherein the compacted article is placed in the gap between two abutting surfaces to dampen vibrations. In general, compacted articles comprising polyelectrolyte complexes may be prepared in which the article's transverse dimensions are no less than about 10,000 nm, no less than about 100 micrometers, no less than about 1 mm, or more, such as no less than about 1 cm, no less than about 2 cm, no less than about 5 cm, or even no less than about 10 cm. For example, a compacted article may be prepared in the shape of a cube or rectangle, in which the transverse dimensions comprise a length, a width, and a thickness, whereby each of these transverse dimensions is no less than about 10 micrometers, no less than about 100 micrometers, no less than about 1 mm, or more, such as no less than about 1 cm, no less than about 2 cm, no less than about 5 cm, or even no less than about 10 cm. Other shapes are possible. For example, the compacted article may be prepared as a sphere, in which the transverse dimension comprises a diameter, whereby the diameter is no less than about 10 micrometers, no less than about 100 micrometers, no less than about 1 mm, no less than about 1 cm, no less than about 2 cm, no less than about 5 cm, or no less than about 10 cm. In yet another alternative, the compacted article may be prepared as a spheroid, either prolate or oblate, in which the transverse dimensions comprise major and minor axes, whereby each of the major and minor axes are no less than about 10 micrometers, no less than about 100 micrometers, no less than about 1 mm, no less than about 1 cm, no less than about 2 cm, no less than about 5 cm, or even no less than about 10 cm.

The percentage pore volume, defined as the total volume of all the pores divided by the total volume of the article x 100%, of a microporous polyelectrolyte complex article may be systematically controlled by mechanically working said article. For example, an article may have a starting porosity of 60% by volume. The article is then doped according to the methods described below to a doping level of at least 0.5. The article is then mechanically worked by kneading, stretching, folding, shearing, compressing, or flowing.

The polyelectrolyte is preferably maintained in a fully hydrated state during the method of the present invention preferably by contact with water. In the fully hydrated state chunks, pellets, pieces or other shapes or articles of microporous polyelectrolyte complex are fully swollen with water, i.e., their water content approaches the maximum it would achieve when immersed in water under the conditions of forming Pieces of complex that are fully hydrated, doped to the preferred level, and wetted by a film of water are suitable for the present invention. Because dried pieces of polyelectrolyte complex are difficult to rehydrate, it is preferred that the microporous polyelectrolyte complex materials be prepared by coprecipitation of individual polyelectrolytes and maintained in a hydrated state, preferably in contact with water.

In one preferred embodiment, the shape of the article at the end of the forming step is defined by the contours of a mold, in the case where the doped polyelectrolyte complex is forced into a mold. If the process starts with a plurality of articles, these articles are fused into a single shape at the end of the process.

In another preferred embodiment, the doped polyelectrolyte is extruded through an orifice, which defines the shape of the cross section of the reshaped article. If the process starts with a plurality of articles, these articles are fused into a single shape at the end of the process, although it is understood that the shape can be cut off with a blade at any point during this preferred embodiment. Methods known to the art for extruding materials, such as forcing materials through a die or orifice via a piston or a screw, are suitable. The orifice may be of any geometry known to the art, including those geometries that enhance the alignment of high-aspect-ratio fillers during the extrusion step. The orifice and other components are preferably made from corrosion-resistant materials, such as stainless steel, plastic or ceramic. For a screw extruder, a continuous form may be produced as long as pieces of polyelectrolyte complex are fed into the extruder continuously. If the starting polyelectrolyte complex article is not doped to the preferred level the pieces of polyelectrolyte complex that are fed into the extruder will not fuse together efficiently.

In another preferred method the doped polyelectrolyte complex article comprises magnetic nanoparticles and a force is applied by a magnetic field, preferably of field strength in the range 0.1 to 60 Tesla, more preferably 1 to 10 Tesla, to draw the complex into a mold or through an orifice. During this preferred method, the magnetic domains are advantageously aligned. Preferred methods for applying a force may be combined. For example, a magnetic field may be applied in a direction perpendicular to, or parallel to, the direction of the force applied by hydrostatic pressure, and simultaneously with the hydrostatic pressure.

The temperature during the forming step preferably does not differ widely from room temperature. Preferably the temperature is between 0° C. and 100° C. More preferably, the temperature is between 20° C. and 80° C. and yet more preferably the temperature is between 20° C. and 60° C. For polyelectrolyte complexes comprising biological molecules which must be maintained close to physiological conditions the temperature during the forming step is preferably maintained at 37° C. plus or minus 10° C.

The preferred conditions lead to the preferred doping level within the polyelectrolyte complex article that is to be shaped. The temperature may be increased to above room temperature to control the doping level for a polyelectrolyte complex article in contact with a solution with a fixed salt concentration. It has been shown (Bucur et al. Journal of the American Chemical Society 2006, vol 128, p. 13690) that the doping effectiveness for a particular salt increases as temperature increases. The doping effectiveness is quantified by an equilibrium doping constant, Kd. For example, Kd increases from about 0.7 to about 2 on going from 4° C. to 60° C. for sodium nitrate doping of a PDADMA/PSS complex article. Thus, it is not "melting" but an increase in doping effectiveness that is responsible for an increased ability to form a polyelectrolyte complex article when it is fully hydrated with water. The preferred doping levels are specified without reference to temperature.

General Additives

Additives in general may appear in the solid matrix comprising polyelectrolyte complex, or in the micropores of the article, or in both. The relative amounts appearing the pore phase and in the solid (polyelectrolyte complex) phase depend on the relative affinity of the additives to the pore and solid phases.

Solid additives that may be incorporated into the polyelectrolyte complex are typically known to the art to modify the physical properties of materials. Additives include fillers and/or reinforcing agents and/or toughening agents, such as inorganic materials such as metal or semimetal oxide particles (e.g., silicon dioxide, aluminum oxide, titanium dioxide, iron oxide, zirconium oxide, and vanadium oxide), clay minerals (e.g., hectorite, kaolin, laponite, montmorillonite), hydroxyapatite, or calcium carbonate. For example, nanoparticles of zirconium oxide added to a polyelectrolyte solution or complex solution tend to improve the abrasion resistance of the article. See Rosidian et al., *Ionic Self-assembly of Ultra Hard ZrO$_2$/polymernanocomposite Films*, Adv. Mater. 10, 1087-1091. When a magnetic force is to be applied to reshape the polyelectrolyte complex article preferably comprises magnetic particles having at least one dimension in the size range between 2 nanometers and 100 micrometers. High aspect ratio fillers are preferred for stiffening a microporous article at a relatively low fill loading. Preferred high aspect ratio additives include, metal fibers, needle-like clay minerals, such as attapulgite, and carbon-based fibers such as carbon fibers or single or multiwalled carbon nanotubes. Other high aspect ratio materials having at least one dimension in the nanometer or micrometer range are suitable additives. Such high aspect ratio materials include polymer fibers, such as nylon, aramid, polyolefin, polyester, cotton, and cellulose fibers, as well as cellulose nanofibers. Biodegradable fibers are preferred when the formed polyelectrolyte complex article comprises biodegradable polyelectrolytes. The weight % of additives in the polyelectrolyte complex article depends on many factors, such as the aspect ratio and the degree of modification of physical properties required. Accordingly, the solid additives may comprise between about 1 wt % and 90 wt % of the polyelectrolyte complex article.

Preferably additives are added prior to the preparation of the starting polyelectrolyte complex article. Negatively charge additives are preferably combined with solutions comprising predominantly negatively charged polyelectrolytes prior to mixing with solutions comprising predominantly positively charged polyelectrolytes so that the additives and polyelectrolytes do not associate prematurely. Additives and individual polyelectrolytes are preferably thoroughly mixed in solution first under shear flow (as created by stirring or a homogenizer) with the proviso that the shear rate should not be sufficient to break up the polymer chains. If however, the polyelectrolyte stabilizes and assists in the dispersion of the additive it may be preferable to first mix additive and polyelectrolytes of opposite charge. For example, nanotubes can sometimes be dispersed better in solution if they are "wrapped" with polymers.

For physiological applications of the reshaped polyelectrolyte complex article other additives may be added during the method of the present invention. Articles for use in the wound protection system preferably further comprise physiologically active additives. For example, articles that are to be implanted in vivo may optionally further comprise antibacterial and/or anti-inflammation and/or antirejection agents and/or growth factors. These additives respectively aid in reducing infection, inflammation or rejection of the implanted article. Additives which promote healing are especially preferred. Examples of antibiotics are well known to the art and are to be found in E. M. Scholar, The antimicrobial drugs, New York, Oxford University Press, 2000 or the Gilbert et al., The Stanford Guide to Antimicrobial Therapy, Hyde Park, Vt., 2000, or the R. Reese, Handbook of Antibiotics, Philadelphia, Lippincot, 2000. Antibacterial agents include silver. Other additives are known to the art for promoting various biomedical properties. These include paclitaxel, seratonin, heparin, and anticlotting factors. Unlike additives used to modify the physical properties of the polyelectrolyte complex article, additives with biological or biomedical activity are typically added in lower concentration. Accordingly, such additives preferably comprise between 0.001% and 5% by weight of the polyelectrolyte complex article.

These additives are preferably mixed with one of the constituent polyelectrolytes solutions that are used to prepare the polyelectrolyte complex. The advantage of introducing additives prior to precipitation is that the additives are incorporated more uniformly throughout the polyelectrolyte complex.

Pore Additives

Several additives are advantageously incorporated into the pores of the microporous polyelectrolyte complex article. Said additives may be imbibed into the porous complex after it is prepared, or, more preferably, additives are added to one or more of the polymer solutions as they are mixed or before they are mixed. Such additives benefit from being trapped in pores yet accessible under some conditions to a liquid phase outside of the pores. Additives that inhibit clotting are preferred when the wound protection system is deployed inside the body, such as for immobilizing damaged bone, organs or blood vessels. Additives that promote clotting are preferred when the wound protection system is deployed in an exterior mode, such as protecting a cut to the skin. Preferred additives for the pore phase include organic and inorganic catalysts, including enzymes. An enzyme catalyzes the transformation of a first molecule to another. Often, the first molecule is small. If the first molecule is small enough to permeate the polyelectrolyte complex phase surrounding the pores, it may enter the pores, undergo catalytic transformation, then exit the pores.

Wound Protection System

The preferred system for wound protection, or dressing, or immobilization, comprises a sealed container and a strip of microporous polyelectrolyte complex, "MiPEC," having an equilibrium modulus of at least 1 kPa at room temperature. Said strip of MiPEC is preferably immersed in a solution comprising a salt, wherein the MiPEC is doped at room temperature to a first doping level. The MiPEC may be stored in a container, e.g., packaging. The environment within the container is preferably sterile and the container material is preferably made from a material capable of being sterilized. The container is sealed to the extent that neither water vapor nor any component of the contents of the container may escape, and pathogens may not enter the container. The container itself is preferably in the form of a flexible pouch, preferably made from plastic, that enables the microporous polyelectrolyte complex to be stored with other microporous complexes in the same pouch, or individually. Pouches are preferably flat, occupying the minimum volume, such that numerous pouches may be stored in the minimum volume. The pouch preferably comprises a weak area to enable the user to rip it open quickly.

The dimensions of the strip, or strips, of microporous polyelectrolyte complex depend on the nature of the wound they are to protect. In all cases, the strips are at least 10 micrometers in thickness, preferably at least 100 micrometers in thickness. For example, a strip used to protect a small wound to the finger has a preferred thickness of at least 0.5 mm a width of at least 5 mm and a length of at least 5 cm. These are starting dimensions, and in the normal course of use the strip will be deformed such that one dimension increases at the expense of the others. Thus, following activation, the 5 cm strip may be deformed lengthwise to 10 cm in order to circumferentially enclose the finger, and the thickness and width will decrease accordingly.

A strip used to protect a fracture to a small bone might be of the same dimensions as the strip to protect the finger. A large bone would require a correspondingly larger strip, as would a gash to the leg, to implement the circumferential wrapping or enclosing. A blood vessel, on the other hand, would require more delicate strips of preferred thickness 10-1000 micrometers and other dimensions in the 1-10 mm range.

The dimensions of the MiPEC to be used also depend on whether the wound is to be protected or protected and immobilized. For example, a skin wound might need only 0.5 mm of MiPEC to prevent ingress of dirt and pathogens, but if a bone fracture is to be protected a thick layer of MiPEC.

The preferred MiPEC composition comprises biodegradable polyelectrolytes if it is used within the body.

Preferred Methods of Use for Wound Protection

The preferred methods of use are adapted to situations where wound protection is desired immediately, such as on the battlefield or in the operating theatre. Accordingly, the wound protection system is preferably at hand to the user and is preferably activated, preferably by heating, immediately prior to use. The container is opened and the strip of MiPEC is removed and immediately deformed so as to cover the wound.

Preferably the MiPEC is deformed at least 10% in one dimension, more preferably by at least 50%. In this respect, it is advantageous to apply the deformed MiPEC circumferentially, rather than as a patch. That is, the MiPEC is preferentially wrapped around a limb, organ, vessel or bone such that it wraps back on itself. The MiPEC then seals to MiPEC, forming a complete seal around the wound. The circumferential application of the MiPEC is preferred to applying it as a patch, since MiPEC does not seal to skin well, and would thus need additional adhesive layers of another material added on top is it were used as a patch.

The wound protection system of the current invention offers further advantages for immobilization as well as protection. Specifically, in the example described below, activated, deformable MiPEC may be hardened after it is activated. For example, MiPEC activated by heating to e.g. 50° C. will harden on cooling to 37° C. or lower. Furthermore, since the MiPEC comprises salt, its modulus may be increased by rinsing said salt out. The rinse step can occur artificially, by rinsing with an aqueous solution, or it may occur naturally by rinsing or exposure to bodily fluids.

Methods of Activation

The wound protection system can come pre-activated or it can be activated immediately prior to use. Activation induces doping as defined above such that the MiPEC can be deformed irreversibly. Additional doping causes the MiPEC to become softer and deformable. Preferred methods of on-site activation are done rapidly so that the wound protection system may be rapidly deployed. Methods of activation include heating, increasing the salt concentration within the polyelectrolyte complex from a first salt concentration to a second salt concentration wherein the second salt concentration is higher than the first salt concentration, adding a more strongly-doping salt, or changing the pH (if pH-sensitive polyelectrolytes are employed). Adding a more strongly doping salt means adding a salt comprised of at least one ion, either the cation, the anion, or both having a valence of greater than 1. As explained above, ions having valence greater than 1, e.g., 2, 3, 4, are more strongly doping than ions having a valence of 1. In all cases, the material retains closed-shell porosity so that it continues to exclude pathogens.

A MiPEC that is preactivated with salt and not further activated is preferably treated with a diluting solution after use, since the activated material has deformable/plastic properties. Such a diluting solution removes excess salt and causes hardening. A MiPEC that is preactivated by pH is preferably hardened by a change in pH after use. Preferably, a MiPEC is activated immediately prior to use in the sterile container in which it is preferably supplied.

A MiPEC is preferably activated immediately prior to use by heating. Preferably, the MiPEC is supplied in a container in which the MiPEC is in contact with a solution having salt and other additives, such as alcohol, sufficient to dope the MiPEC to a level above about $y=0.1$ but not above about $y=0.5$ at room temperature. The MiPEC is then activated by heating it to a temperature preferably between 37° C. and 80° C., more preferably between 45° C. and 55° C. The additional heating causes additional doping sufficient to decrease the modulus of the MiPEC such that it may be drawn at least 10% in one dimension, more preferably above 50% in one dimension. The MiPEC is then preferentially wrapped circumferentially around the wounded appendage, organ, vessel or bone before it cools. As it cools, in a matter of seconds, it hardens. The hardened MiPEC is then optionally rinsed, causing it to become even harder.

Activation by heating is preferably done with microwave irradiation. Since the wound protection system comprises water, commercial microwaves operating at the frequency needed to excite water molecules are suitable for use. A microwave is capable of activating the wound protection system within tens of seconds. The microwaves penetrate plastic materials used for the pouch. Microwave ovens are widely available. Optionally, the wound protection system is supplied with a microwave oven manufactured to optimize the heating of the wound protection system.

Other preferred methods of heat activation are via a chemical hot-pack, which releases heat on the mixing of two chemicals, or induction heating. Chemical hot-packs take longer to heat the MiPEC but are more compact than a microwave oven. If heating of several wound protection systems simultaneously is desired, chemical hot-packs are preferred to a single microwave.

Induction heating is possible if the MiPEC further comprises metallic particles or superparamagnetic particles such as iron oxide nanoparticles of diameter less than about 100 nm. Induction heating is also rapid, and requires a radiofrequency power supply.

Sealing the MiPEC

In accordance with the preferred method of use the MiPEC is deformed and wrapped circumferentially around the appendage, organ, vessel, or bone that is injured. During wrapping the MiPEC preferably is at a temperature warmer than physiological (37° C.), is wet with aqueous solution and comprises salt. Under these conditions, the MiPEC will bond with itself. If desired, the ends of the deformed MiPEC required to bind can be heated locally with a hot object to induce further doping and to enhance fusion. Alternatively, the ends of the strip of MiPEC can be moistened with solution containing sufficient concentration of a salt to dope the MiPEC to greater than $y=0.5$. Alternatively, the ends of the MiPEC strip further comprise metallic or superparamagnetic nanoparticles that can be locally heated by radiofrequency induction heating.

Simultaneous Cauterizing

Cauterization is often employed on wounds. Cauterization helps to stem bleeding and kills pathogens locally. Cauterization may be performed chemically or by heat. Thus, one preferred aspect of the present invention is to apply the wound protection system at a temperature and/or salt concentration that induces cauterization.

On the other hand, cauterization by heat or chemicals can be painful. Thus, if cauterization, or osmotic shock, is to be avoided the salt used to dope the MiPEC comprises ions that dope the MiPEC at close to physiological osmotic strength (isotonic). For example, while 1 M NaCl is used on the PSS/PDADMA MiPEC in Example 5, the ionic strength is higher than physiological (ca. 0.15 M NaCl). This concentration of salt will cauterize, via osmotic shock, tissues, but will be painful. However, calcium chloride or magnesium chloride dopes the MiPEC to the same y levels at lower ionic strength.

Biocompatibility

It has been shown that certain polyelectrolytes or polymers are biocompatible. For example, a biocompatible polyelectrolyte multilayer, on which smooth muscle cells were grown, has been described by Schlenoff et al (U.S. Pub. No. 2005/0287111) which is herein incorporated by reference. This multilayer comprised fluorinated polyelectrolyte complex, on which cells grow. However, the cells do not consume the fluorinated material. In one aspect of the present invention, therefore, the formed polyelectrolyte complex article further comprises a surface stratum of fluorinated polyelectrolyte. The surface stratum is preferably obtained by immersing the microporous polyelectrolyte complex article in a solution of fluorinated polyelectrolyte. The process may be repeated with alternating positive and negative fluorinated polyelectrolytes to obtain a thicker surface stratum. In one embodiment, the alternating layering to build up the surface stratum comprising fluorinated polyelectrolyte may be repeated to deposit between about one and about 1000 positively and negatively charged fluorinated polyelectrolyte pairs, preferably between about one and about 250 positively and negatively charged fluorinated polyelectrolyte pairs.

Bioinertness

It has been shown that a polyelectrolyte complex film comprising a zwitterion repeat unit has bioinert properties, i.e., the adsorption of proteins, cells and other biological materials is minimized on the film. Examples are provided in U.S. Pub. No. 2005/0287111). Therefore, in one aspect of the present invention, the formed polyelectrolyte complex article further comprises a surface stratum comprising polyelectrolytes comprising zwitterionic repeat units. Other bioinert materials are known to the art, such as poly(ethylene glycols), PEG. Therefore, in one aspect of this invention, the microporous polyelectrolyte complex article further comprises a surface stratum of PEG.

Other biological materials are known to be biocompatible, such as serum albumin. In one embodiment, the formed polyelectrolyte complex article may be coated with serum albumin on exposure to in vivo conditions (i.e. following implant).

Modulus

The Young's modulus, E, (also known as elastic modulus, modulus of elasticity, or tensile modulus) is a measure of the stiffness of a material. E is the ratio between the tensile stress, σ, divided by the tensile strain, e. E is typically measured on a tensile apparatus which elongates a material and reports the stress needed to produce a certain strain. Alternatively, a sample is compressed and the required stress for a needed deformation is measured. E may be measured under static, or quasi-static, conditions, where the stress does not vary with time. Alternatively, the modulus can be measured under dynamic or time-varying conditions where a material may exhibit properties of elasticity and viscous flow (viscoelasticity) in which case the modulus depends on frequency of deformation and a complex modulus, E*, is defined, where $E^*=E_1+iE_2$, where $E_1$ is the storage modulus, which is a measure of energy stored on a deformation cycle, and $E_2$ is the loss modulus, which is a measure of the energy lost on a cycle.

The shear modulus, G, (also referred to as the modulus of rigidity) of a material, measured under dynamic or time-varying conditions, is the ratio of the shear stress to the shear strain. The shear modulus is typically measured with a parallel-plate rheometer. If the shear rate changes, G depends on the frequency at which the shear changes. Therefore, a complex shear modulus is defined as $G^*=G_1+iG_2$, where $G_1$ is the storage modulus, which is a measure of energy stored on a deformation cycle, and $G_2$ is the loss modulus, which is a measure of the energy lost on a cycle. For isotropic materials, $E=3G$ for small deformations. For the present purposes, a material with low E is termed "soft" while a material with low G is termed "flowable."

The ratio $E_1/E_2$ or $G_1/G_2$ is equal to $\tan(\Delta)$, the ratio of energy lost to energy stored in one cycle. $\tan(\Delta)$ is called the loss factor and is a measure of damping efficiency, with greater damping indicated by higher $\tan(\Delta)$.

Damping or shock-absorbing properties are not determined from static measurements. Damping properties are ascertained by time varying or periodic deformation of the sample. Thus, a soft material (low E) is not necessarily a good candidate for damping. Furthermore, a material that is effective for damping over a certain frequency range may not be effective for damping over another frequency range. Therefore, in reporting a complex modulus (E* or G*), a frequency or frequency range is preferably specified.

The equilibrium modulus, $E_o$ or $G_o$, is defined as the modulus at zero frequency, or infinite time, when the viscous contributions to the modulus have been allowed to dissipate and all that remains is an elastic component.

The descriptor "stable" applied to microporous polyelectrolyte complex articles indicates that the article retains its shape when not under load, and deforms but retains a second shape when placed under load. In other words, the article exhibits a minimal $E_o$ under a specific set of conditions, and retains elastic character during normal use. The microporous polyelectrolyte complex article described herein preferably has an equilibrium shear modulus greater than 1 kPa at 25° C. when immersed in an aqueous solution of 0.15M NaCl.

In general, the complex shear modulus of a microporous polyelectrolyte complex of the present invention may vary between about 1 kPa and about 400 MPa, such as between about 1 MPa and about 20 MPa, between frequencies of about 0.1 Hz and 10,000 Hz. The complex shear modulus of the microporous polyelectrolyte complex depends, at least in part, on five factors: the chemical composition of polyelectrolytes, the pore size and distribution, the overall pore volume, the salt ions, and the concentration of salt within the bulk of the polyelectrolyte complex. For example, G* of a nonporous article comprising poly(styrene sulfonate) (PSS) and poly(diallyldimethylammonium) (PDADMA) decreases between about 2 MPa and about 0.1 MPa per 0.1 M increase in ionic concentration within the bulk of the article at about 10 Hz. In another example, G* of a microporous article comprising polymethacrylic acid and PDADMA decreases with increasing sodium chloride as shown in the following Table V. In Table V, the values of G* at various frequencies for the nucleus pulposus of the human lumbar intervertebral disc are shown for comparison. Advantageously, the viscoelastic behavior of an intervertebral disc of the pulposus may be reproduced by a microporous poly(methacrylic acid)/poly (diallyldimethylammonium) (PMAA/PDADMA) polyelectrolyte complex article.

TABLE V

Comparison of Complex Shear Modulus Behavior of Nucleus Pulposus and Microporous Polyelectrolyte Complex

| Material | W (rad/s) | \|G*\| | Δ (deg) |
|---|---|---|---|
| Nucleus pulposus[1] | 1 | 7.40 ± 11.6 | 23 ± 5 |
| | 10 | 11.30 ± 17.9 | 24 ± 5 |
| | 100 | 19.8 ± 31.4 | 30 ± 6 |
| PMAA/PDAD | 1 | 3.2 | 38 |
| 0.15M | 10 | 7.5 | 30 |
| | 100 | 15.2 | 25 |
| PMAA/PDAD | 1 | 7.3 | 32 |
| 0.00M | 10 | 15.0 | 27 |
| | 100 | 27.2 | 23 |

[1] (from J. S. Iatridis et al, J. Biomechanics, 30, p. 1005-1012 (1997))

In one embodiment, the complex shear modulus of a compacted article comprising polyelectrolyte complex prepared in a solution comprising between about 0.1 M and about 0.5 M sodium chloride may, after equilibration, be between about 0.1 MPa and about 5 MPa over a frequency range of 0.1 to 1000 Hz. A microporous article having a complex shear modulus within this range may be loaded into a cavity, such as an intervertebral disk space, through a cannula. Preferably, the polyelectrolyte complex is prepared in a solution having a higher sodium chloride concentration, such as between about 0.15 M and about 0.30 M, more preferably about 0.25 M, to yield an article having a G* near the lower end of the stated range, which yields a more flowable and more easily injected article. Potassium chloride achieves a greater decrease in G* for a given concentration than does sodium chloride. Accordingly, preferred potassium chloride salt concentrations are between about 0.1 M and about 0.4 M, such as between about 0.15 M and about 0.3 M.

For applications requiring the insertion of microporous article comprising polyelectrolyte complex in vivo, as a medical implant, it is not advantageous to use salt concentrations significantly higher than 0.15 M. This is because the osmotic pressure can shock surrounding tissue. However, it is advantageous to introduce the compacted object having a more flowable character and allow it to harden in vivo. For this purpose, it is preferable to employ a salt of calcium, aluminum or magnesium, preferably the chloride or citrate salt, in the centrifugal compaction process at physiological osmotic pressure, introduce the implant, then allow the implant ions to be replaced by physiological ions (i.e. mostly NaCl). Microporous complexes comprising substantially salts of calcium, aluminum or magnesium are more flowable than compacted complexes comprising NaCl at the same ionic strength.

If large changes in ionic strength are to be avoided, it is preferable to use a salt of calcium, aluminum, or magnesium preferably the citrate, chloride, or bromide during the compaction step. The use of salts other than sodium chloride is preferred when the ionic strength of NaCl required for good compaction is greater than about 2 M. As the concentration of salt increases the density of the solution increases. The higher solution density leads to less efficient centrifugal compaction. Therefore, the use of another salt, having improved compaction properties at lower concentration, is preferred. Examples of said alternative salts include those from calcium, aluminum, or magnesium.

Microporous articles comprising polyelectrolyte complex exhibit good shape memory. The porosity allows the article to be reversibly deformed to a much greater extent. If an article is to be used for mechanical damping, it is desirable that any mechanical deformation of the article induced by transient stress be completely reversible. That is, when the stress is removed from the article it recovers its original dimensions. If the original dimensions are recovered instantly the article is said to be elastic. If the original dimensions are recovered over time, the article exhibits viscoelastic response. If the article does not recover its original dimensions, it is irreversibly deformed. For example, an article comprising a nonporous complex of PDADMA/PSS exhibited reversible deformation up to 2% strain, whereas a microporous article comprising the same polymers and 80% micropore volume could be reversibly deformed by more than 100%. Such deformation/recovery cycling is sometimes termed "shape memory." The mechanical behavior of an intervertebral disk is viscoelastic. Therefore, the present invention advantageously reproduces the mechanical properties of a disk.

A preferred application of the microporous article comprising polyelectrolyte complex is as a replacement for soft skeletal material, particularly the disks between spinal vertebrae. The material may also be employed as cartilage replacement for other cartilage materials, such as that found in the knee joint.

One example of an artificial intervertebral disk is the Charite™ artificial disk by DePuy Spine Inc., approved by the FDA in 2004. This disk comprises polyethylene sandwiched between metal plates. While the Charite disk allows natural spine flexion, the modulus of the materials used is much higher than that of a natural intervertebral disk such that the artificial disk does not have the same damping (shock absorption) properties.

One approach to replacing disks is to fill intervertebral cavities with a natural polyelectrolyte complex comprising cells that will form new tissue. Cells have been immobilized in polyelectrolyte gels. For example, Lim and Sun (Science, 210:908-910 (1980)) described Islets of Langerhans immobilized in natural polyelectrolytes (alginate gels). There are several potential problems with this. First, natural polyelectrolyte gels tend to be very low modulus and cells take time to grow into fully functional tissue. Thus, the patient will not be able to place full mechanical load on the growing disk before it has fully formed. Second, natural polyelectrolytes, such as chitosan and hyaluronic acid are substrates for cell metabolism. They may be metabolized too quickly and by other cells. Third, nerve cells can grow into disks, which create pain. For these and other reasons, the compacted article of the present invention preferably comprises at least one polyelectrolyte comprising synthetic or non-natural repeat units. The synthetic repeat units are less likely to be degraded/consumed in vivo.

As can be seen from the examples below, microporous polyelectrolyte complexes have favorable complex shear modulii. For example the poly(styrene solfonate)/poly(diallyldimethylammonium) (PSS/PDADMA) complex has a G* of about 15 MPa in 0.15M NaCl. This compares favorably with the modulus of a complete intervertebral disk of 1 MPa to 25 MPa.

An intervertebral disk comprises the nucleus pulposus (an interior gel), and the annulus fibrosus (which is tougher and fibrous). Commonly, the annulus tears and the nucleus leaks out. The disk loses thickness and damping capability and may impact the spinal cord or cause irritation. Optionally, the nucleus pulposus is replaced by a microporous polyelectrolyte complex article. The polyelectrolyte complex is soft but will not leak out. The additional material added to the disk will separate the vertebrae, reducing deformities of the spine.

Optionally, the microporous article comprising polyelectrolyte complex is injected into the intervertebral space by means of a needle or cannula. In this procedure, the vertebrae are mechanically stabilized with clamps. Polyelectrolyte complex disk material is injected between vertebrae. Excess salt is then washed away with excess saline solution. The disks are allowed to harden and then the clamps are removed after all the excess salt is washed away.

In some applications, such as the replacement of an intervertebral disk, the microporous article preferably comprises higher modulus material on the outside or periphery or surface stratum of the article and a lower modulus in the interior region of the article. The lower modulus in the interior or interior region serves to absorb more shock, and the higher modulus in the periphery or surface region serves to retain the shape and integrity of the microporous article comprising polyelectrolyte complex. Accordingly, in one aspect of this invention, there is a gradient in modulus within the microporous article. Such a gradient may be accomplished using various approaches. Preferably, the gradient is produced by a gradient in percent pore volume. For example, the inner region comprises a higher pore volume, giving a lower modulus, than the outer region.

To produce a gradient within a microporous polyelectrolyte complex article the composition is changed as material is injected into the cavity. For example, a syringe is loaded with a gradient material wherein the material closest to the needle has the highest modulus. Material further from the needle has lower modulus. Therefore, high modulus material is injected first, followed by the low modulus material. During injection, the bolus of injected low modulus material inflates the high modulus material. At the end of the injection, the resulting article comprises an inner region with lower modulus and an outer region with higher modulus.

Another preferred method of forming a gradient in modulus is by forming a gradient in additives. For example, when injecting the microporous polyelectrolyte complex into a cavity a material comprising fibrous additives, preferably biocompatible additives, is injected first. Then, material which comprises a lower proportion of fibrous additive is injected. The resulting microporous article comprises a surface region with fibrous additives and an inner region without fibrous additives (or a lower percent of said additives).

In order to produce a gradient in percent pore volume for an injected microporous polyelectrolyte complex article the less porous material is preferably injected into a cavity first followed by the more porous material.

Another preferred method of producing a surface region with a modulus that is different than the interior region is by crosslinking polyelectrolyte located in the surface region of the article. Crosslinking is accomplished by heat treatment, by infusing crosslinking agents into the article from the outside in, or by photocrosslinking the article. The advantage of photocrosslinking the microporous article is that the penetration depth of the light into the article may be controlled by the wavelength selected, such that the crosslinking occurs only within thin surface region on the external surface of the article. Preferably the modulus of the surface region of the article comprising polyelectrolyte complex is at least 2 times greater, preferably at least about 5 times greater, even more preferably at least about 10 times greater than the modulus of the bulk region of the article.

Having described the invention in detail, it will be apparent that modifications and variations are possible without departing from the scope of the invention defined in the appended claims.

EXAMPLES

The following non-limiting examples are provided to further illustrate the present invention.

In the examples, the following shorthand for polyelectrolyte complexes built on substrates is employed: $(A/B)_x$ where A is the starting polyelectrolyte contacting the substrate, B is the terminating polyelectrolyte in contact with subsequent protein solutions and x is the number of layer pairs. In $(A/B)_xA$, A would be the terminating polymer. Salt, MY (cation M and anion Y), has an important role in the buildup process and is represented by $(A/B)_x$ @ c MY, where c is the molarity of the salt (MY) in the polymer solution. The pH can be included in the nomenclature esp. when using pH dependent polyelectrolytes. For example, $(PAH/PAA)_2PAH$ @ 0.25 M NaCl @ pH 7.4, represent two layers pairs of PAH/PAA built at 0.25 M NaCl and a pH of 7.4.

Example 1

Static Stress-Strain Behavior of a Nonporous Polyelectrolyte Complex

Nonporous polyelectrolyte complexes were prepared by the method of multilayering on a Teflon™ (perfluoropolymer) substrate. For the purposes of this invention, nonporous polyelectrolyte complex articles are defined as those articles comprising less than 1 volume % of pores of average diameter greater than 100 nanometers. These articles were tested to compare to the mechanical properties of porous polyelectrolyte complexes. Nonporous polyelectrolyte complexes were exposed to salt solutions of various concentrations for durations sufficient to equilibrate the bulk salt concentration of the polyelectrolyte complex with the salt solution. After equilibration, the elastic moduli of the nonporous polyelectrolyte complexes were measured.

Poly(styrene sulfonic acid) (PSS, molecular weight $6.8 \times 10^4$, $M_w/M_n=1.06$) and poly(diallyldimethylammonium chloride) (PDADMA, molecular weight $3.7 \times 10^5$, $M_w/M_n=2.09$) were obtained from Aldrich. Sodium chloride (NaCl) was obtained from Fisher. Deionized water (Barnstead, E-pure, Milli-Q) was used to prepare all aqueous solutions.

Two polyelectrolyte solutions were prepared, one comprising PSS and one comprising PDADMA. The polyelectrolyte concentration was 0.01 M (with respect to the monomer repeat unit) and the sodium chloride concentration was 1.0 M.

The poly(tetrafluoroethylene) (Teflon™) substrate (50 mm length×24 mm width×1.6 mm thickness) was cleaned in ethanol. The PDADMA/PSS nonporous polyelectrolyte complex was built upon the substrate according to the multilayer method by alternately exposing the substrate to the two polymer solutions for 5 minutes using a robotic platform (StratoSequence, nanoStrata Inc.) with three rinses of deionized water for 1 minute each. Rinse and polymer solution volumes were 50 mL. The polyelectrolyte complex was annealed at room temperature in a sodium chloride solution (1.0 M) for one week.

The "dry" thickness of the multilayer was determined using Fourier Transform Infrared Spectroscopy (FTIR) comparison (using the strong sulfonate stretch at $1100 \text{ cm}^{-1}$) of a PDADMA/PSS nonporous polyelectrolyte complex of known thickness (measured with a Gaertner Scientific L116S ellipsometer).

The PDADMA/PSS polyelectrolyte complex was peeled off the Teflon™ substrate using flat-ended tweezers and cut into microcoupons (2.0 mm length×150 μm width×9.0 μm dry thickness) with a razor blade. Both ends of a microcoupon were wrapped around aluminum foil clips and secured thereto by applying a drop of silicone rubber before closing the clips.

The aluminum clips were connected to minuten pin hooks on a capacitance-type force transducer (3.3 kHz resonant frequency; Aurora Scientific, Ontario, Canada, calibrated with small weights), and a moving iron galvanometer motor (step times≤300 μs; Aurora Scientific, Ontario, Canada), designed for monitoring contractile behavior of single muscle fibers, mounted on the base of a Leitz Diavert (Wetzlar, Germany) inverted microscope. Silicone sealant was used to stabilize the clips on the minuten pins. Position was monitored by a capacitance-type transducer in the motor. Calibration was done by applying a control voltage input (square wave) to the motor, and measuring (using a microscope) the linear distance traveled in the horizontal plane by a clip attached to the motor hook. This allowed for rapid determination of the delta-position for a given input wave amplitude.

A temperature controlled stage containing six salt solutions of variable ionic strength (0.0 M, 0.2 M, 0.4 M, 0.6 M, 0.8 M. and 1.0 M sodium chloride) was used to soak the polyelectrolyte complex microcoupons for in situ measurements. Using these solutions at room temperature provides respective doping levels in the nonporous complex of about 0.0, 0.15, 0.25, 0.3, 0.35 and 0.45. Under these conditions the polyelectrolyte complex article was elastically deformed. The salt solutions were held in 200-μL anodized aluminum wells. The temperature was maintained at 28±1° C. with an ATR-4 regulator (Quest Scientific, North Vancouver, BC, Canada). Before every measurement, the polyelectrolyte complex microcoupon was conditioned in the salt solution for 10 minutes. Experimental control, data collection, and analysis of raw data were carried out using a PC-based system with a DT2831-G board (Data Translation, Marlboro, Mass.) and custom software. The software performs a fast Fourier transform method, converts to polar notation, finds the maximum amplitude index, calculates stiffness values and phase shift values, writes them to a file, converts to complex notation, and performs an inverse fast Fourier transform. Force was normalized to the polyelectrolyte complex microcoupon cross-sectional area, which was calculated from the wet thickness at different salt concentrations.

FIG. 1 shows the stress-strain behavior of the nonporous (PDADMA/PSS)$_{250}$@1.0M NaCl polyelectrolyte complex at different salt concentrations. The curves correspond to salt concentrations as follows: (open circle) 0.0 M NaCl solution; (asterisk) 0.2 M NaCl solution; (triangles) 0.4 M NaCl solution; (crosses) 0.6 M NaCl solution; (squares) 0.8 M NaCl solution; (diamonds) 1.0 M NaCl solution correspond to the stretching cycle (in increasing order of elongation) while (solid circles) 0.0 M NaCl solution; (solid triangles) 0.4 M NaCl solution; and (solid squares) 0.8 M NaCl solution indicate a decreasing elongation cycle.

Figure 2:
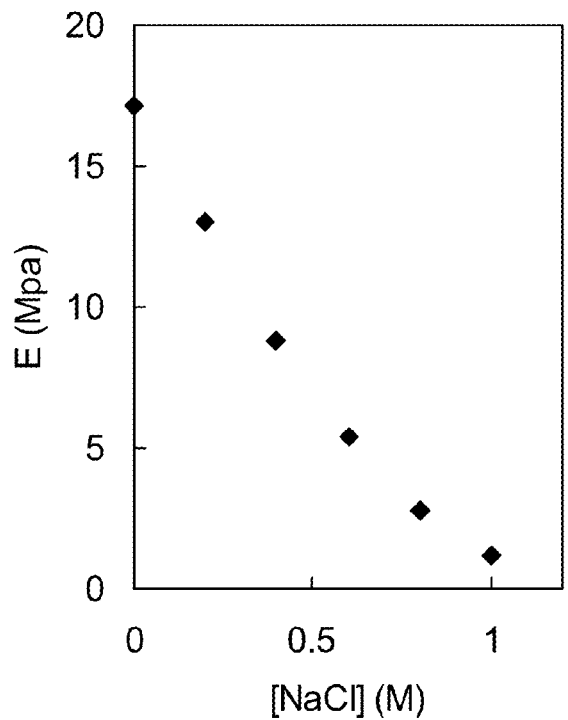
FIG. 2 is a graph depicting the elastic modulus of a nonporous polyelectrolyte complex after conditioning at several ionic strengths. The data were obtained from the slope of the curves in FIG. 1. At 0.0 M NaCl, E=17 MPa. The data in the graph were obtained according to the method of Example 1.

FIG. 2 shows the elastic modulus, E, of the (PDADMA/PSS)$_{250}$@1.0M NaCl polyelectrolyte complex at different salt concentrations. The elastic modulus is obtained from the slope of the curves in FIG. 1. At 0.0 M NaCl, E=17 MPa. Elastic modulus, E, measures the resistance to deformation of a material when stress is applied. Elastic modulus is defined according to the following equations:

$$E = \frac{\sigma}{e}$$
$$e = \frac{L - L_0}{L_0}$$

wherein e is the strain, σ is the stress, and $L_0$ and L are the length of the polyelectrolyte complex at rest and the length of the polyelectrolyte complex after applying a certain strain, respectively.

In agreement with these Equations the relationship between applied strain and resulting stress in polyelectrolyte complex for e<2% (i.e., percent of elongation less than 2% of length of polyelectrolyte complex at rest) was found to be linear. Further, when the elongation cycle was repeated at a certain ionic strength, $\sigma_{eq}$ was reproducible with minimal hysteresis. This means that the multilayer recovered almost completely when the applied strain is removed (i.e. there was no residual deformation).

Elastic modulus, E, evaluated from the slopes of the stress-strain data as show in FIG. 2, was observed to decrease as the ionic strength increased. That is, the polyelectrolyte complex material becomes softer as more salt is added.

Example 2

Dynamic Storage Modulus of Nonporous Polyelectrolyte Complexes

The damping behavior of nonporous polyelectrolyte complex was tested. Polyelectrolyte complex ((PDADMA/PSS)$_{250}$@1.0M NaCl) microcoupons prepared according to the method described in Example 1 were subjected to a series of uniaxial sinusoidal strains, e, elongating the polyelectrolyte complex by 1% of their original length. The applied strain is within the region of linear viscoelastic behavior where the measured stress is directly proportional to the strain. The experiment was carried out in situ with microcoupons immersed in salt solutions of different ionic strength, and the ensuing dynamic stress, a, was recorded.

Figure 3:
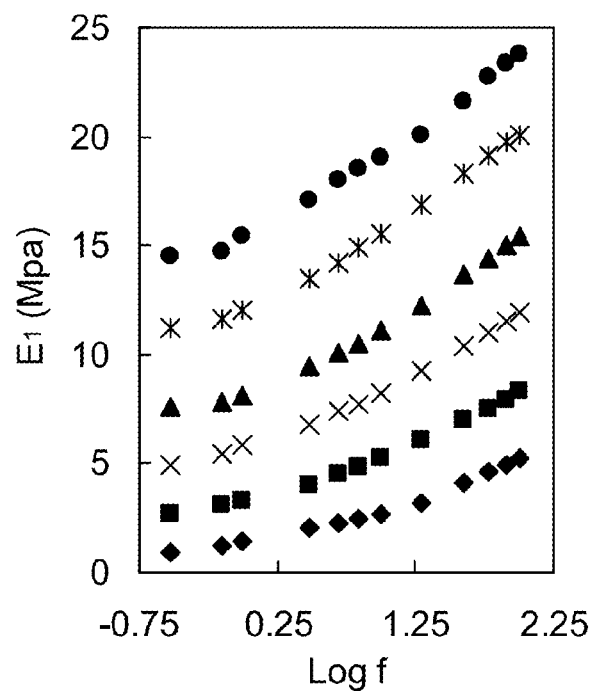
FIG. 3 is a graph showing the Dynamic Storage Modulus behavior of a nonporous polyelectrolyte complex (PDADMA/PSS multilayer) as a function of frequency (Hz) after conditioning at several ionic strengths. Circles, asterisk, triangles, crosses, squares and diamonds correspond to salt concentrations of 0.0, 0.2, 0.4, 0.6, 0.8 and 1.0M NaCl respectively. Strain amplitude was 1%. The stress was corrected for actual cross-sectional area of the microcoupons, with consideration of water volume fraction. The data in the graph were obtained according to the method of Example 2.

When a polyelectrolyte complex microcoupon was oscillated sinusoidally (frequency, f=0.1-100 Hz), at constant ionic strength, the relationship between $E_1$ and f showed two distinct regions. See FIG. 3, which shows the dynamic storage modulus behavior of the (PDADMA/PSS)$_{250}$@1.0M NaCl polyelectrolyte complex at different salt concentrations as a function of frequency (Hz). The curves correspond to salt concentrations as follows: (solid circles) 0.0 M NaCl solution; (asterisks) 0.2 M NaCl solution; (solid triangles) 0.4 M NaCl solution; (crosses) 0.6 M NaCl solution; (solid squares) 0.8 M NaCl solution; (solid diamonds) 1.0 M NaCl solution. The stress was corrected for actual cross-sectional area of the microcoupons, with consideration of water volume fraction.

At low frequency (0.1-1.0 Hz), the polyelectrolyte complex had enough time to reorient to a new lower free energy state before the next deformation cycle, such that the complex exhibits rubber-like behavior. At high frequency (f>1.0 Hz) or at short time, the polymer chains do not have enough time to relax, such that the complex exhibits glassy behavior.

Example 3

Dynamic Loss Modulus of Nonporous Polyelectrolyte Complexes

The energy dissipation behavior of nonporous polyelectrolyte complex was tested. Nonporous polyelectrolyte complex ((PDADMA/PSS)$_{250}$@1.0M NaCl) microcoupons prepared according to the method described in Example 1 were subjected to a series of uniaxial sinusoidal strains, e, elongating the polyelectrolyte complex by 1% of their original length. The applied strain is within the region of linear viscoelastic behavior where the measured stress is directly proportional to the strain. The experiment was carried out in situ with microcoupons immersed in salt solutions of different ionic strength, and the ensuing dynamic stress, a, was recorded.

Figure 4:
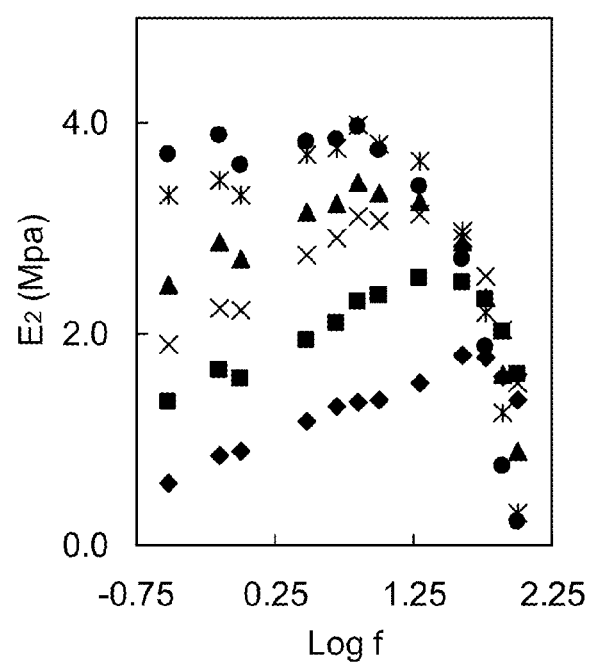
FIG. 4 is a graph showing the Dynamic Loss Modulus behavior of a nonporous polyelectrolyte complex (PDADMA/PSS multilayer) as a function of frequency (Hz) after conditioning at several ionic strengths. Circles, asterisk, triangles, crosses, squares and diamonds correspond to salt concentrations of 0.0, 0.2, 0.4, 0.6, 0.8 and 1.0M NaCl respectively. Strain amplitude was 1%. The stress was corrected for actual cross-sectional area of the microcoupons, with consideration of water volume fraction. The data in the graph were obtained according to the method of Example 3.

FIG. 4 depicts the isothermal loss modulus spectra of the polyelectrolyte complex immersed in the salt solutions of various ionic strengths. The curves correspond to salt concentrations as follows: (solid circles) 0.0 M NaCl solution; (asterisks) 0.2 M NaCl solution; (solid triangles) 0.4 M NaCl solution; (crosses) 0.6 M NaCl solution; (solid squares) 0.8 M NaCl solution; (solid diamonds) 1.0 M NaCl solution. The stress was corrected for actual cross-sectional area of the microcoupons, with consideration of water volume fraction. According to FIG. 4, $E_2$, was also found to be a function of the rate of the applied strain and the salt concentration of the bathing medium.

In contrast to the low frequency region, where $E_2$ increased with frequency, irrespective of solution ionic strength, the loss modulus deteriorated toward the high frequency end of the spectrum. However, as the salt concentration decreased below 1.0 M, the loss modulus peak broadened progressively. Since $E_2$ is directly proportional to $E_1$ ($E_2=E_1$ Tan Δ), the whole curve shifted towards a lower value of $E_2$ when the ionic strength of the medium increased.

When different systems are compared at the same strain amplitude, $E_2$ serves as a measure of the energy dissipated per cycle. Typically, viscoelastic polymers show $E_2$ values in the range of 0.03-0.05 MPa at 1-10 Hz. At the same frequency range, the polyelectrolyte complex has a loss modulus of 0.5-1.5 MPa and 3.5-4.0 MPa at 1.0 and 0.0 M NaCl respectively. Therefore polyelectrolyte complexes exhibit significant increases in energy dissipation compared to conventional viscoelastic materials.

Example 4

Loss Factor of Nonporous Polyelectrolyte Complexes

The damping properties of nonporous polyelectrolyte complex were tested. Nonporous polyelectrolyte complex ((PDADMA/PSS)$_{250}$@1.0M NaCl) microcoupons prepared according to the method described in Example 1 were subjected to a series of uniaxial sinusoidal strains, e, elongating the polyelectrolyte complex by 1% of their original length. The applied strain is within the region of linear viscoelastic behavior where the measured stress is directly proportional to the strain. The experiment was carried out in situ with microcoupons immersed in salt solutions of different ionic strength, and the ensuing dynamic stress, a, was recorded.

In dynamic modulus analysis, the strain will be out of phase with the stress (i.e., viscoelastic lag) due to the time necessary for molecular rearrangements. Accordingly, it is possible to probe the extent of damping in polyelectrolyte complexes via the phase angle, A.

Figure 5:
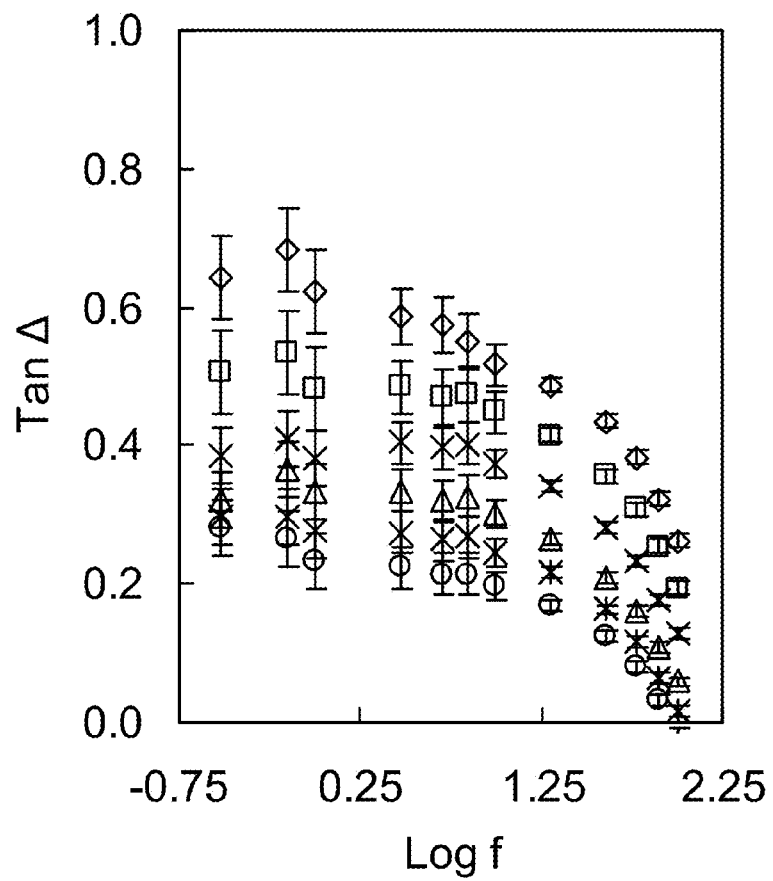
FIG. 5 is a graph showing the damping behavior of a nonporous polyelectrolyte complex after conditioning at several ionic strengths. Circles, asterisk, triangles, crosses, squares and diamonds correspond to salt concentrations of 0.0, 0.2, 0.4, 0.6, 0.8 and 1.0M NaCl respectively. Solid lines are guides to the eye. The data in the graph were obtained according to the method of Example 4.

FIG. 5 depicts the damping behavior of polyelectrolyte complex immersed in the salt solutions of various ionic strengths. The curves correspond to salt concentrations as follows: (open circles) 0.0 M NaCl solution; (asterisks) 0.2 M NaCl solution; (open triangles) 0.4 M NaCl solution; (crosses) 0.6 M NaCl solution; (open squares) 0.8 M NaCl solution; (open diamonds) 1.0 M NaCl solution. Solid lines are guides to the eye.

FIG. 5 shows quantitatively that the polyelectrolyte complex was able to dissipate a larger fraction of energy at higher ionic strength. The effect of ionic strength and applied frequency on the damping ability of the multilayer can be summarized as follows: In the low frequency region (0.3-10 Hz), Tan($\Delta$) remained fairly constant, especially at salt concentrations above 0.2 M. It started to decline at about 20 Hz and progressively deteriorated as the multilayer response became more glassy-like (f>20 Hz). As the salt concentration decreased, damping was observed to diminish.

Example 5

Preparation of Microporous Polyelectrolyte Complex Using an Ultracentrifuge

A microporous article comprising polyelectrolyte complex was prepared. Two solutions were prepared, each comprising polyelectrolyte. One solution was prepared by dissolving poly(diallyldimethylammonium chloride) (PDADMAC, 10 wt. %) and sodium chloride (2.5 M) in water. One solution was prepared by dissolved poly(styrene sulfonate) (PSS, 10 wt. %) and sodium chloride (2.5 M) in water. The solutions were mixed in a beaker and stirred with the aid of a magnetic stir bar. A gelatinous precipitate formed.

The precipitate was allowed to settle and most of the supernatant was poured off. The precipitate was placed in a centrifuge tube, and the tube place in a type TL series 90 Ti rotor. The rotor was placed in a Beckman ultracentrifuge, and the precipitate was centrifuged at 25° C. at 55,000 rpm for 4 hours. An optically transparent solid compact plug of microporous polyelectrolyte complex formed at the bottom of the tube, and the excess liquid was poured off. The plug was removed and cut with a razor blade into shapes for mechanical testing.

Example 6

Frequency Dependent Modulus Studies on Microporous Polyelectrolyte Complex

Appendix A (containing additional examples below) describes the synthesis and modulus measurements on two microporous polyelectrolyte complexes. It should be noted that the equilibrium modulii of the microporous PSS/PDADMA polyelectrolyte complexes described in Appendix A (pore volume approximately 70%) are orders of magnitude LOWER than those disclosed above for nonporous PSS/PDADMA polyelectrolyte complexes. The polymers used to make the porous and nonporous complexes were the same (same source and same molecular weight).

Example 7

Proof of Porous Structure

Figure 6:
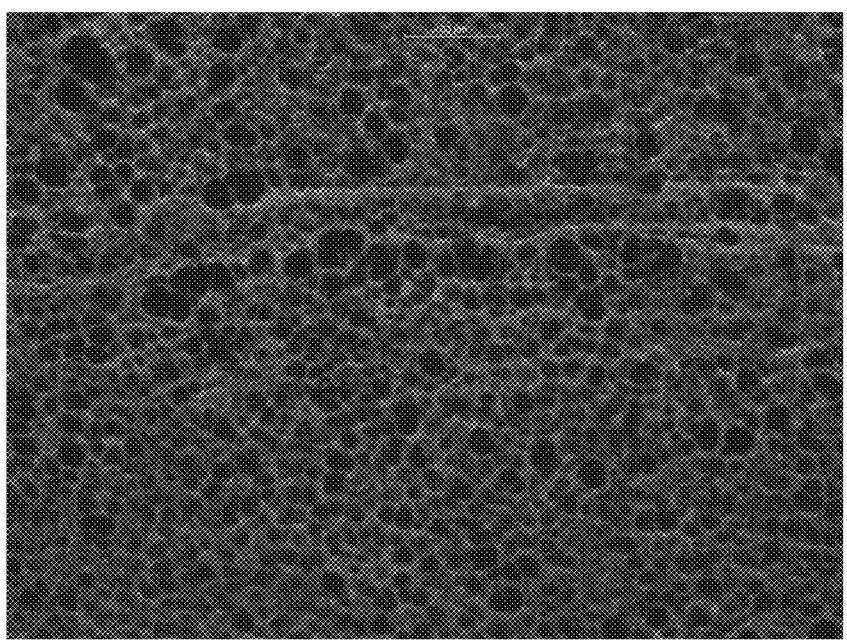
FIG. 6 is an optical micrograph of a 10 micrometer thick slice of a microporous polyelectrolyte complex article (PSS/PDADMA prepared from 2.5 M NaCl) showing a plurality of pores of diameter in the 10-100 micrometer range. The article was prepared according to the method described in Example 5.

In this example, a microporous polyelectrolyte complex article was prepared according to Example 5 and a microtome was used to slice the sample into slices 10 micrometers thick. FIG. 6 depicts an optical micrograph of one of these slices. The Figure depicts a complex with approximately 80% pore volume. The pores are of diameter in the tens of micrometers. The polyelectrolyte complex forms a solid phase around the pores. Each pore is thus enclosed by a membrane of polyelectrolyte complex. There was absolutely no reason to expect that a polyelectrolyte complex shaped by ultracentrifugation should comprise micropores.

Example 8

Proof of Closed Shell Pores

A piece of microporous polyelectrolyte complex prepared according to Example 5 was immersed in 0.1 M NaCl in water. This sample was known to contain a 12% (by weight) excess of PSS (compared to PDADMA) located in the micropores. The solution above the complex was monitored with ultraviolet absorption spectroscopy at 250 nm to detect the presence of PSS. After 7 days no significant PSS was detected.

Another piece of microporous polyelectrolyte complex prepared according to Example 5 was immersed in 0.1 M NaCl in water. Each day this sample was chopped into smaller pieces with a razor blade. In this case up to 2% by weight of the PSS in the complex was observed in the solution above the complex. Clearly, the razor blade had cut through some of the closed pores, releasing some PSS trapped therein.

Example 9

Activation and Deformation of Microporous Polyelectrolyte Complex

A MiPEC prepared according to Example 5 was cut to have dimensions of 10 mm×5 mm×1 mm and it was immersed in 1.0 M NaCl in water. The NaCl solution was heated to approximately 50° C. at which point the modulus of the MiPEC decreased by about a factor of 10. It was quickly extended and wrapped completely around a finger, circumferentially, sealing on itself. After it cooled, the MiPEC formed a tight seal. The simulated wound dressing was then rinsed in distilled water for 1 minute, whereupon the modulus increased further and slight shrinkage was observed.

APPENDIX A

Modulus Measurements on Microporous Polyelectrolyte Complex Articles

This appendix A contains additional examples on the preparation of articles comprising porous polyelectrolyte complexes. Hydrogels are water-swollen polymeric networks. See Peppas, N. A. Hydrogels in Medicine and Pharmacy, Vol. 3: Properties and Applications; CRC Press: Boca Raton, 1987; Bao, Q. B.; McCullen, G. M.; Higham, P. A.; Dumbleton, J. H.; Yuan, H. A. Biomaterials 1996, 17, 1157-1167; Thomas, J.; Lowman, A.; Marcolongo, M. J. Biomed. Mat. Res. A 2003, 67A, 1329-1337; and Hutmacher, D. W. J. Biomat. Sci. Polym. Ed. 2001, 12, 107-124. Crosslinks are introduced either by covalent bonding or by physical interactions of secondary binding forces, such as hydrogen bonding, Coulombic interactions, or van der Waals forces. Covalent gels are stable, whereas physical gels exhibit a greater sensitivity to the conditions of the surrounding environment. In covalent gels the number of crosslinks is irreversible, whereas in the physical gels it can be tuned with the pH, temperature or the ionic strength. Soft biological tissues, such as cartilage or intervertebral disks, are based on hydrogel matrices comprising extensive physical crosslinks. See Muir, H. Bioessays 1995, 17, 1039-1048; Roughley, P. J.; Lee, E. R. Microsc. Res. Tech. 1994, 28, 385-397; and Bao, Q. B.; McCullen, G. M.; Higham, P. A.; Dumbleton, J. H.; Yuan, H. A. Biomaterials 1996, 17, 1157-1167.

Macroscopic polyelectrolyte gels of chitosan, hyaluronan, and alginate have been studied for medical and pharmaceutical applications, such as drug delivery, wound healing or cell immobilization. See Petrak, K. J. Bioact. Compat. Pol. 1986, 1, 202-219. In the early 90's, Decher and co-workers described a method for constructing ultrathin films of polyelectrolyte complex using pairs of oppositely charged polyelectrolytes. See Decher, G.; Hong, J. D. Berichte Bunsen-Gesellschaft Phys. Chem. 1991, 95, 1430-1434; and Decher, G.; Lvov, Y.; Schmitt, J. Thin Solid Films 1994, 244, 772-777. This versatile technique consists of the alternating deposition of polyelectrolytes on a substrate, resulting in so-called polyelectrolyte multilayers, PEMUs. Planar films or capsules have been obtained depending on the geometry of the substrate. See Decher, G.; Schlenoff, J. B. Multilayer Thin Films: Sequential Assembly of Nanocomposite Materials, 2003; and Decher, G. Science 1997, 277, 1232-1237. PEMUs have been deposited on surfaces to improve the biocompatibility of materials and to control the behavior of cells grown on them. See Podsiadlo, P.; Paternel, S.; Rouillard, J. M.; Zhang, Z. F.; Lee, J.; Lee, J. W.; Gulari, L.; Kotov, N. A. Langmuir 2005, 21, 11915-11921; Boura, C.; Menu, P.; Payan, E.; Picart, C.; Voegel, J. C.; Muller, S.; Stoltz, J. F. Biomaterials 2003, 24, 3521-3530; Salloum, D. S.; Olenych, S. G.; Keller, T. C. S.; Schlenoff, J. B. Biomacromolecules 2005, 6, 161-167; Schneider, A.; Francius, G.; Obeid, R.; Schwinte, P.; Hemmerle, J.; Frisch, B.; Schaaf, P.; Voegel, J. C.; Senger, B.; Picart, C. Langmuir 2006, 22, 1193-1200; Olenych, S. G.; Moussallem, M. D.; Salloum, D. S.; Schlenoff, J. B.; Keller, T. C. S. Biomacromolecules 2005, 6, 3252-3258.

The density of crosslinks in a gel determines its mechanical properties. PEMUs are essentially a thin-film nonporous morphology of polyelectrolyte complexes, PECs, where the crosslinks are created by ion pairing between oppositely charged repeat units on polyelectrolytes. The density of these ion pair crosslinks depends on the salt concentration of the solution to which they are exposed. See Michaels, A. S.; Miekka, R. G. J Phys Chem 1961, 65, 1765-1773; Michaels, A. S. Ind. Engin. Chem. 1965, 57, 32-40; and Sukhishvili, S. A.; Kharlampieva, E.; Izumrudov, V. Macromolecules 2006, 39, 8873-8881. By increasing the salt concentration of this solution, crosslinks between polymer/polymer ion pairs, or "intrinsic" sites, are broken and replaced by polymer/counterion pairs, or "extrinsic" sites. This "doping" of a polyelectrolyte complex with a univalent salt can be described by the following equilibrium:

$$Pol^+Pol^-_c + A^-C^+_{aq} \leftrightarrows Pol^+A^-_c + Pol^-C^+_c \qquad [1]$$

where $Pol^+$ and $Pol^-$ are respective polycation and polyanion repeat units, and $A^-$ and $C^+$ the associated counter ions. The subscript c refers to components in the complex phase. See Dubas, S. T.; Schlenoff, J. B. Langmuir 2001, 17, 7725-7727. The equilibrium doping, or swelling, constant, $K_{dop}$, is defined as:

$$K_{dop} = \frac{y^2}{(1-y)a_{A^-}a_{C^+}} \qquad [2]$$

where a is the activity of the relevant ion, and y and 1-y are the respective fractions of extrinsic and intrinsic sites. The salt concentration is a powerful tool to control the crosslinking density, and therefore the material properties, of PECs. In the 60's, Michaels and others reported the swelling and the progressive transition of nonporous polyelectrolyte complexes from a glassy state to a rubbery one when exposed to electrolyte solutions. See Michaels, A. S.; Miekka, R. G. J Phys Chem 1961, 65, 1765-1773; Michaels, A. S. Ind. Engin. Chem. 1965, 57, 32-40; and Yano, O.; Wada, Y. J Appl. Pol. Sci. 1980, 1723. Yet no quantitative mechanical measurements were reported. More recently, the softening effect of salt has been described for various PEMUs. See Lebedeva, O. V.; Kim, B.-S.; Vasilev, K.; Vinogradova, O. I. J. Coll. Interfac. Sci. 2005, 284, 455-462; Jaber, J. A.; Schlenoff, J. B. J Am. Chem. Soc. 2006, 128, 2940-2947; Jaber, J. A.; Schlenoff, J. B. Chem. Mat. 2006, 18, 5768-5773; Lulevich, V. V.; Vinogradova, O. I. Langmuir 2004, 20, 2874-2878; and Heuvingh, J.; Zappa, M.; Fery, A. Langmuir 2005, 21, 3165-3171. Herein, a systematic measurement of the static mechanical properties of a PEMU according to classical theories of rubber elasticity is described.

We recently reported favorable mechanical damping properties for PEMUs. See Jaber, J. A.; Schlenoff, J. B. Chem. Mat. 2006, 18, 5768-5773. While reproducible, dense, films of nonporous PEC are routinely available by the multilayering method, when the same polyelectrolytes are mixed in solution to produce solution-precipitated PECs in larger quantities the products are diffuse blobs. In the present work, we describe a processing method for producing large-scale, resilient, formable articles of microporous polyelectrolyte complex which are suitable for bioimplants. We term these complexes microporous polyelectrolyte complexes, MiPECs. The immediate targets are replacement materials for connective structures between bones, which need to be tough, elastic, hydrated, and biocompatible. In addition, their mechanical properties should mimic as closely as possible those of the tissue (in the healthy state) they are replacing. In our method, we subject complexes to significantly higher salt concentrations than those they would experience during their intended application. Doping, per Equation 1, by the additional salt ions induces plasticization, temporarily breaking the ion pairs and allowing the complex to flow under a centrifugal field. When the extreme salt concentration is removed, the complexes revert to a higher-modulus, elastic state. To demonstrate the potential for in vivo use of MiPECs, we show that a MiPEC made with poly(methacrylic acid) (PMAA) and PDADMAC exhibits properties similar to those of the nucleus pulposus of an intervertebral disk. See Iatridis, J. C.; Setton, L. A.; Weidenbaum, M.; Mow, V. C. *J. Biomech.* 1997, 30, 1005-1013.

Materials and Methods

Poly(4-styrenesulfonic acid) ($M_w$=7.5×10$^4$ g/mol, $M_w/M_n$=1.4) and poly(diallyldimethylammonium chloride) ($M_w$=40×10$^4$-50×10$^4$ g/mol, $M_w/M_n$=2.09) were both used as received from Aldrich. Poly(methacrylic acid) ($M_w$=8.0×10$^4$ g/mol) was purchased from Scientific Polymer Products. Sodium chloride (Fisher) was used to vary the ionic strength. All solutions were prepared in deionized water (Barnstead, E-pure, Milli-Q). For PSS/PDADMA, polyelectrolyte solutions were 0.5 M (with respect to the monomer unit) in 2.5 M NaCl. The pH of the solutions was adjusted to between 6.5-7.0 with 1M NaOH or HCl. Complexes were prepared by mixing 20 mL of each polyelectrolyte solution under stirring. Precipitates were centrifuged using polycarbonate thick wall centrifuge tubes and an ultracentrifuge (Beckman XL-90) equipped with a type 70Ti rotor (tube angle 25°, Beckman) at 188,000 g for 4 hours at 25° C. The MiPECs made in 2.5 M NaCl were immersed in NaCl solutions with concentrations ranging from 0.00 M to 2.5 M for 48 hours. PMAA/PDADMA MiPECs were prepared in the same way, except the concentrations of the polyelectrolyte solutions were fixed at 0.3 M, the pH was adjusted to 7.0 and MiPECs were made directly in Milli-Q water without any added salt as the salt released from the complexation produced a physiologically relevant ionic strength of ca. 0.15 M NaCl. These MiPECs were annealed in 0.15 M NaCl.

Weight measurements allowed the determination of water and salt content in the MiPECs annealed under different [NaCl]. The mass of a MiPEC in the swollen state is the sum of the masses of polymers, salt (counter ions) and water:

$$m^s_{CoPEC}(x) = m_{polymer} + m_{NaCl}(x) + m_{H_2O}(x) \quad [3]$$

where $m_{polymer}$, $m_{NaCl}(x)$, and $m_{H_2O}(x)$ are the respective contributions of the polymer, the salt and the water as a function of salt concentration, x. The index s refers to the swollen state. While the mass of the polymer is independent of solution salt concentration, the water and the salt content vary. The water content of the complex was determined for each salt concentration by drying (110° C. under vacuum to constant mass):

$$m_{H_2O}(x) = m^s_{CoPEC}(x) - m^d_{CoPEC}(x) \quad [4]$$

where the index d refers to the dry state. The salt content can be estimated from the difference in dry weight between salt-swollen and water-rinsed (x→0) MiPECs:

$$m_{NaCl}(x) = m^d_{MiPEC}(x) - m^d_{MiPEC}(0) \quad [5]$$

MiPECs were cut into pieces of $m^s_{MiPEC}(x)$ in the range 1 to 3 g and dabbed dry with a paper wipe before weighing. These pieces of gel were immersed in 50 mL of water for 2 days before weighing them to obtain $m^s_{MiPEC}(0)$. Some samples before and after immersion in water were dried at 80° C. under vacuum for 2 h to determine the water content $m_{H_2O}(x)$ for each salt concentration. All experiments were repeated twice.

Mechanical shear tests were carried out on a controlled stress and strain Bohlin Gemini 150 rheometer with a parallel plate configuration (diameter=20 mm) in a humidity enclosure chamber. Temperature was maintained at 37.0±0.1° C. Control and data collection were carried out with Bohlin software R6.50.5.6.

A compressive strain of about 10% was applied to ensure gripping of the samples and full planar contact. A relaxation time of a few minutes allowed the axial force to approach equilibrium. Dynamic oscillatory shear experiments, based on the sinusoidal variation of the strain (γ) and the stress (Φ) with an angular frequency (ω), allowed the determination of the viscoelastic properties of MiPECs. The sinusoidal shear strain signal is $\gamma = \gamma_0 e^{i\omega t}$. If the value of $\gamma_0$ is small enough, the corresponding shear stress output is $\sigma = \sigma_0 e^{i\omega t}$. This is the linear viscoelastic region (LVR) of the material. The complex shear modulus (G*) can be defined for the material as:

$$G^* = \sigma_0/\gamma_0 \text{ and } G^* = G' + iG'' \quad [6]$$

where G' is the storage modulus and G" the loss modulus, representing respectively the real and the imaginary part of the complex shear modulus. The linear viscoelastic properties can be also described by the values of the magnitude of the shear complex modulus (|G*|) and the phase shift angle (δ) between the stress and the strain, $$|G^*| = |G'^2 + G''^2|^{1/2} \text{ and } \tan(\delta) = G''/G' \quad [7]$$

The value of |G*| gives a measure of the shear stiffness of the material under dynamic conditions. Tan(δ) indicates the elastic or viscous nature of the material. δ varies between 0° (Hookean solid) and 90° (Newtonian fluids). See Ferry, J. D. *Viscoelastic Properties of Polymers.* 2nd ed, Wiley, New York, 1970. A dynamic angular frequency sweep ($5 \times 10^{-4} \leq \omega \leq 188$ rad/s) was achieved using a value of $\gamma_0$ located in the LVR for all the frequency ranges. Samples for microscopy were sectioned by microtome under cryogenic conditions and images were recorded, while the PEC was immersed in water, on a Nikon Eclipse Ti microscope equipped with a photometrics CoolSNAP HQ$^2$ camera at 100× magnification.

Results and Discussion

Saloplasticity

All solid materials exhibit some combination of viscous and elastic response when deformed. In a permanently networked polymer a force exists that will restore the material to its original dimensions when stress is removed. Thus, the decades-old observation of "rubbery" properties in polyelectrolyte complexes does not necessarily imply that PECs can be formed into new shapes. See Michaels, A. S. *Ind. Engin. Chem.* 1965, 57, 32-40. For irreversible deformation into new shapes with similar mechanical properties, crosslinks must be broken and remade. Due to the reversible salt-induced control of (physical) crosslink density, it is possible to remove crosslinks during processing.

An additional requirement for processing is that residual crosslinks must be able to break and reform under the time scale of the reshaping step. This implies a certain amount of interdiffusion in PECs. It is known that the addition of salt permits "frozen" polyelectrolyte complexes to become more mobile. A classic example is the exchange of polymers in a solution of "quasisoluble" polyelectrolyte complexes—the addition of salts transforms the complex from nonlabile (no exchange) to labile. See Kabanov, V. A., 2003. Chapter 2. Similarly, we have demonstrated polyelectrolyte interdiffusion on the surface, and in the bulk, of PEMUs in the presence of salt. See Dubas, S. T.; Schlenoff, J. B. *Langmuir* 2001, 17, 7725-7727 and Jomaa, H. W.; Schlenoff, J. B. *Macromolecules* 2005, 38, 8473-8480.

Temperature is a convenient and traditional parameter for molding polymeric materials. Thermoplastic polymers flow above a glass or melting transition temperature. We have not found any evidence of such thermal transitions in PECs (using differential scanning calorimetry on hydrated samples, data not shown), which are essentially polymeric salts, although higher temperature would certainly enhance interdiffusion and doping of PECs. See Bucur, C. B.; Sui, Z.; Schlenoff, J. B. *J. Am. Chem. Soc.* 2006, 128, 13690-13691. Doping by salt provides an alternate processing parameter, unique to materials held together by ion pairing crosslinks. Since salt does for PECs what temperature does for thermoplastics, we term the salt-induced softening of PECs "saloplasticity." Definition: a saloplastic material comprises ionic crosslinks and may be permanently reshaped when sufficient crosslinks are broken, for example by exposure to a solution of sufficiently high salt concentration.

The degree of doping required for saloplastic deformation of a PEC probably depends on a number of variables, such as hydrophilicity and charge density of the constituent polymers. For the PSS/PDADMA system it was empirically found that solution NaCl concentrations greater than about 2M at r.t were required to efficiently reshape the complex. Using $K_{dop}=0.27$ for NaCl, and approximating activities for concentration, yields γ~0.63 for 2M NaCl and γ~0.7 for 2.5 M NaCl. See Schlenoff, J. B.; Rmaile, A. H.; Bucur, C. B. *J. Am. Chem. Soc.* 2008, 130, 13589-13597. It is likely that whatever conditions of salt concentration, salt type, solvent, temperature, and polymers, are chosen, y should be substantially greater than 0.5 for saloplasticity.

Composition of a PSS/PDADMA MiPEC

Centrifugation is commonly used to separate PECs from the aqueous phase, but the product is simply an opaque, amorphous blob of roughly the same consistency as the precipitate. During a solid-state NMR experiment we spun a PSS/PDADMA sample in 2 M salt at several kHz. After the sample was removed we noticed it had been transformed into a clear, amber plug. The centrifugal fields described in the Experimental section are ultrahigh (>$10^5$ g) and the PEC turns from a diffuse, off-white, scattering blob into a solid, tough, transparent, solid that can be cut into shapes.

Figure 7:
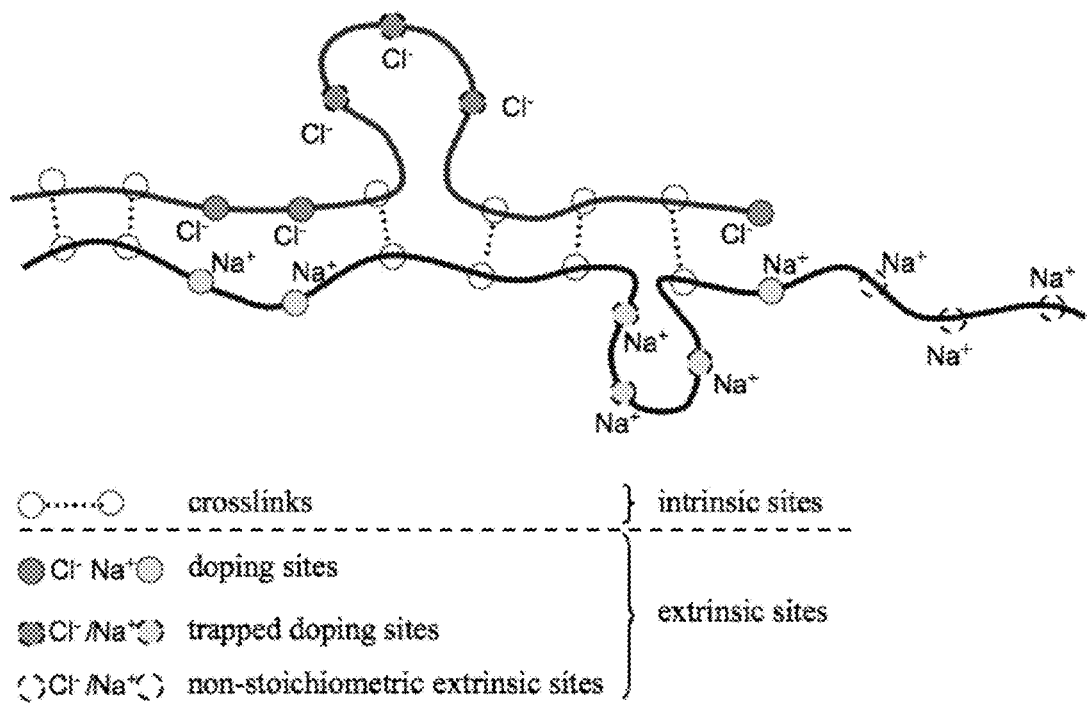
FIG. 7 is an illustration depicting charge compensation in a polyelectrolyte complex.
Figure 8:
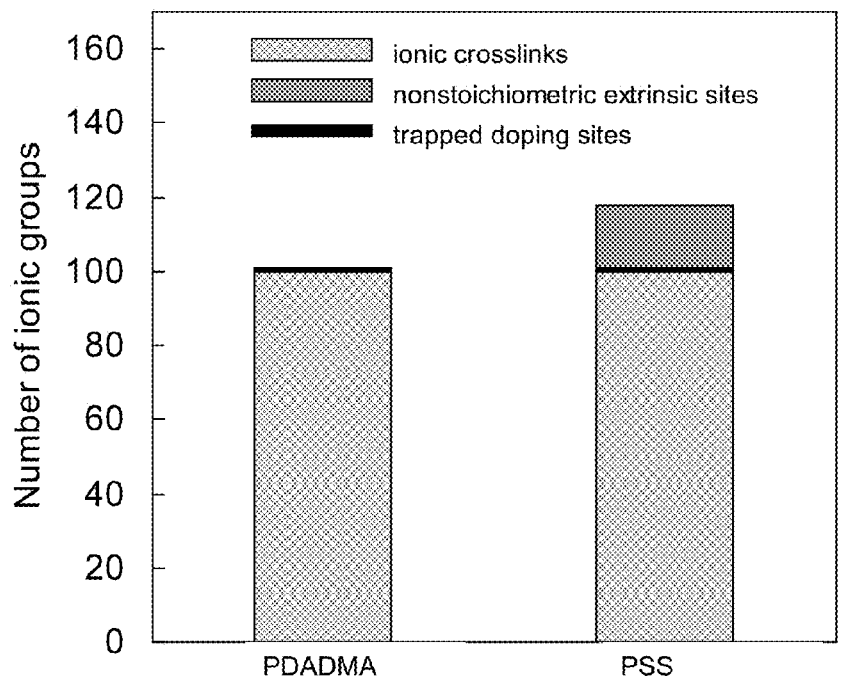
FIG. 8 is a bar chart representation of all types of charge compensation in a dried PSS/PDADMA complex. Crosslinks are paired polyelectrolyte repeat units. Doping sites are reversibly formed extrinsic charge according to Equation 1. Trapped doping sites are extrinsic sites where the polyelectrolyte charges cannot pair because of kinetic constraints on reorganizing polymer chains. Non-stoichiometric extrinsic charge results from non-1:1 stoichiometry of polyelectrolytes in the complex. In this case, PSS is in excess.

MiPECs are composed of a polymer matrix, counter ions (salt), and water. Charges on polyelectrolytes are compensated either by a repeat unit from the oppositely-charged partner (intrinsic) or by salt counterions (extrinsic). Extrinsic sites can have different origins. Some of the extrinsic sites are due to the doping of the crosslinks in the gel network as Equilibrium [1] predicts. Additional extrinsic sites are introduced by a non-stoichiometric ratio between the polyelectrolyte ionic groups. Understanding the properties of a PEC requires comprehensive knowledge of the distribution of extrinsic vs. intrinsic sites. Elemental analysis was performed on a dried PSS/PDADMAC MiPEC sample, prepared under 2.5 M NaCl, and rinsed in water for 48 h. The amounts of sulfur and nitrogen were 9.84 wt % and 3.7 wt %, respectively, corresponding to a molar ratio of 1.17:1 PSS:PDADMA. In other words, the PSS/PDADMA MiPEC made at 2.5 M NaCl exhibits a 17% molar excess (based on the polyelectrolyte repeat units) of PSS, contrary to the 1:1 ratio expected for polyelectrolyte complexation. See Dautzenberg, H.; Jaeger, W.; Kötz, J.; Philipp, B.; Seidel, C.; Stscherbina, D. *Polyelectrolytes: Formation, Characterization and Application*; Hanser: Munich, 1994. Furthermore, a small quantity of chloride, 0.62 wt %, was also revealed in the elemental analysis. The presence of chloride in PEC annealed in water was surprising, since all the ionic groups of the PDADMA were expected to be involved in a crosslink. This chloride content suggests the presence of some residual doping sites in the polymer matrix, possibly resulting from some topological constraints that hinder the formation of a crosslink. FIG. 7 is an illustration depicting charge compensation in a polyelectrolyte complex. FIG. 8 presents all the possible interactions between the ionic groups carried by the polyelectrolyte chains in the PEC matrix. The distribution of the ionic groups of both polyelectrolytes is also given for a given number of 100 crosslinks.

In PECs, including PEMUs, the ratio between the opposite ionic groups is usually assumed to be close to 1:1, though some structural studies have indirectly indicated significant non-stoichiometry. See Schmitt, J.; Gruenewald, T.; Decher, G.; Pershan, P. S.; Kjaer, K.; Löshe, M. *Macromolecules* 1993, 26, 7058-7063; and Riegler, H.; Essler, F. *Langmuir* 2002, 18, 6694-6698. Kabanov and Dautzenberg et al. state that non-stoichiometric PECs require specific experimental conditions, such as a strong difference in molecular weight between polyelectrolytes, significant non-stoichiometry in addition, or high dilution, none of which are present in our system. See Dautzenberg, H.; Jaeger, W.; Kötz, J.; Philipp, B.; Seidel, C.; Stscherbina, D. *Polyelectrolytes: Formation, Characterization and Application*; Hanser: Munich, 1994. is not possible to use elemental analysis to determine the ratio between the ionic groups of each polyelectrolyte since only small amounts of material (ng to μg) are available in multilayers. Using radioanalytical methods, we found no residual salt and thus concluded that the polyelectrolyte stoichiometry in a multilayer built in 0.1 M NaCl was 1:1. See Schlenoff, J. B.; Ly, H.; Li, M. *J. Am. Chem. Soc.* 1998, 120, 7626-7634. This finding was somewhat contradicted by our subsequent FTIR measurements of counterions in PSS/PDADMA PEMUs built in 1.0 M NaCl, which revealed about 3 mol % residual salt. See Farhat, T. R.; Schlenoff, J. B. *J. Am. Chem. Soc.* 2003, 125, 4627-4636. In the MiPEC, prepared in 2.5 M NaCl, this percentage is greater and lies around 18% (trapped doping sites and non-stoichiometric sites). It is possible that non-stoichiometry in PECs (and PEMUs) becomes more significant at higher salt concentrations. Indeed, we found that PSS partially precipitated in 4.5 M NaCl, whereas PDAMAC remained soluble at this same [NaCl], suggesting that concentrated NaCl solutions are worse solvents for PSS than for PDADMAC.

Water and Salt Content for a PSS/PDADMA MiPEC

Water and salt contents of a PSS/PDADMA MiPEC treated with NaCl solutions of concentrations varying from 0.00 M to 2.5 M were determined by weight measurements. The masses of wet and dry materials for doped and undoped PEC are known and the difference yields water and salt content (see Experimental). The total mass of a MiPEC, $m_{MiPEC}(x)$, which varies with salt concentration (Equation 3), was normalized to the mass of the dry MiPEC treated with pure water, $m^d_{MiPEC}(0)$, which corresponds to the mass of the polymer matrix plus the residual salt contained in the non-stoichiometric extrinsic sites and the doping trapped sites. On soaking in pure water the number of crosslinks is at a maximum (see Equation 2). Since no dissolution of the MiPEC was observed in the different treatment solutions, this mass can be assumed to be constant. The weight ratios are defined as:

$$r_{H2O}(x) = \frac{m_{H2O}(x)}{m^d_{CoPEC}(0)} \text{ and } r_{NaCl}(x) = \frac{m_{NaCl}(x)}{m^d_{CoPEC}(0)} \qquad [8]$$

Figure 9:
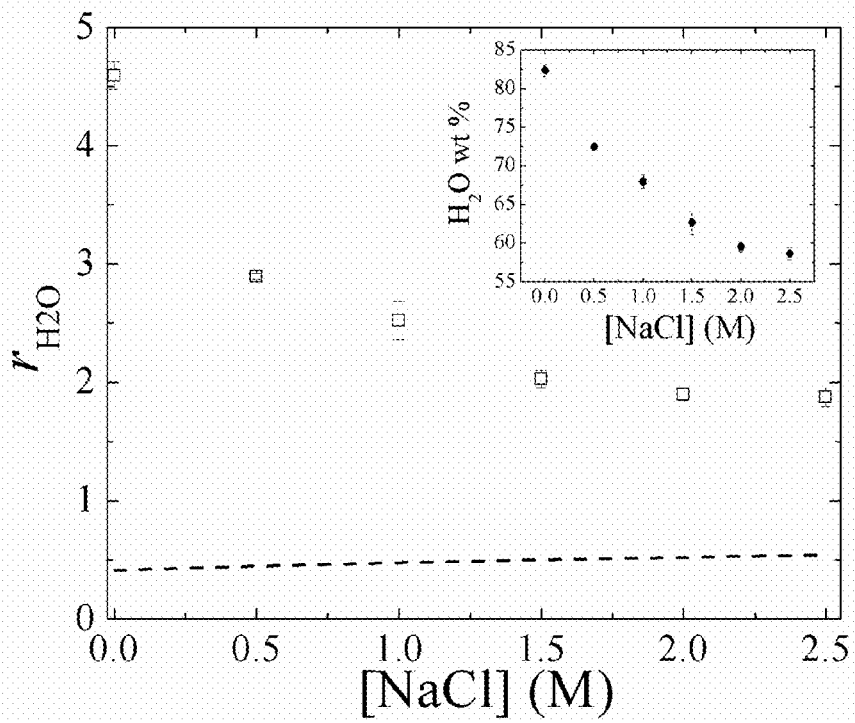
FIG. 9 is a graph depicting the weight ratio of water to polymer content for PSS/PDADMA MiPEC treated with NaCl solutions of various concentration (□). The inset (●) shows water content as a weight % of the MiPEC. The dashed line is the theoretical weight ratio that comes from hydrating the polyelectrolyte ion pairs only (6.9 H$_2$O per polyelectrolyte ion pair and 5.6 H$_2$0 per counterion-compensated site). The difference between the experimental and the theoretical values is due to the presence of the pores.

As shown in FIG. 9, total water content as a function of [NaCl] ranges from 60% to 80%. By comparison, the quantity of water contained in a PSS/PDADMA PEMU built at 1.0 M NaCl is usually lower and is around 30%. See Schlenoff, J. B.; Rmaile, A. H.; Bucur, C. B. *J. Am. Chem. Soc.* 2008, 130, 13589-13597. PEMUs based on hydrophilic polyelectrolytes that can diffuse rapidly over several microns into the film during construction exhibit higher water content values: around 75% at 0.15 M NaCl. See Burke, S. E.; Barrett, C. J. *Biomacromolecules* 2005, 6, 1419-1428; and Porcel, C.; Lavalle, P.; Ball, V.; Decher, G.; Senger, B.; Voegel, J. C.; Schaaf, P. *Langmuir* 2006, 22, 4376-4383. A high water content makes MiPECs suitable for use as replacements for soft biological tissues that exhibit similar water contents.

$r_{H2O}(x)$ decreases from about 5 for pure water to 2 in 2.5M NaCl, meaning the matrix of PSS/PDADMA made at 2.5 M NaCl can absorb between 2 and 5 times its weight of water by varying the salt concentration of the solution to which it is exposed. This value can be compared to a theoretical one calculated using the composition of the polymer matrix determined previously with the elemental analysis, and by taking a water of hydration of 6.9 molecules $H_2O$ per crosslink and 5.6 $H_2O$ per extrinsic sites. See Schlenoff, J. B.; Rmaile, A. H.; Bucur, C. B. *J. Am. Chem. Soc.* 2008, 130, 13589-13597. A $K_{dop}$ of 0.27 was used to calculate hydration water from doping the PSS/PDADMA MiPEC. A large difference between the experimental and theoretical values can be observed. This difference is due to the presence of pores in the complex. A micrograph of a 10 µm slice of PSS/PDADMA MiPEC in water is shown in FIG. 6.

Extensive porosity is clearly observed. As the salt concentration increases, the volume of the pores decreases. These are roughly the same size as micrometer diameter PEMU capsules, which were shown to exhibit excess osmotic pressure inside the capsule due to excess polyelectrolyte. See Vinogradova, O. I.; Andrienko, D.; Lulevich, V. V.; Nordschild, S.; Sukhorukov, G. B. *Macromolecules* 2004, 37, 1113-1117. It is possible that the pores in FIG. 6 contain much of the excess PSS, which generates a differential osmotic pressure (relative to solution) at lower salt concentrations. Given the propensity of polyelectrolytes to pair 1:1 (at lower salt concentrations) and to phase separate, by pore formation or decomposition, it is also reasonable to suppose that excess PSS appears on the inner surface of the pores. See Sui, Z.; Schlenoff, J. B. *Langmuir* 2004, 20, 6026-6031.

We found similar dehydration of PSS/PDADMA multilayers (they have minimal pore volume) with increasing [NaCl], but at sufficiently high salt concentration the PEMU was rehydrated because of the additional water brought into the film by doping. See Jaber, J. A.; Schlenoff, J. B. *Langmuir* 2007, 23, 896-901; and Schlenoff, J. B.; Rmaile, A. H.; Bucur, C. B. *J. Am. Chem. Soc.* 2008, 130, 13589-13597. For the MiPEC described in FIG. 9, the starting water content is simply too high for the doping process to rehydrate the PEC. Any water not directly hydrating polyelectrolytes is considered pore water. From FIG. 9, the polymer hydration water increases slightly, but remains at r~0.5. The pore volume is given by $$\frac{4_{H2O} - 0.5}{4_{H2O} + d^{-1}} \times 100\% \quad [9]$$

where d is the density of PSS/PDADMA (ca. 1.2 g cm$^{-3}$).

Figure 10:
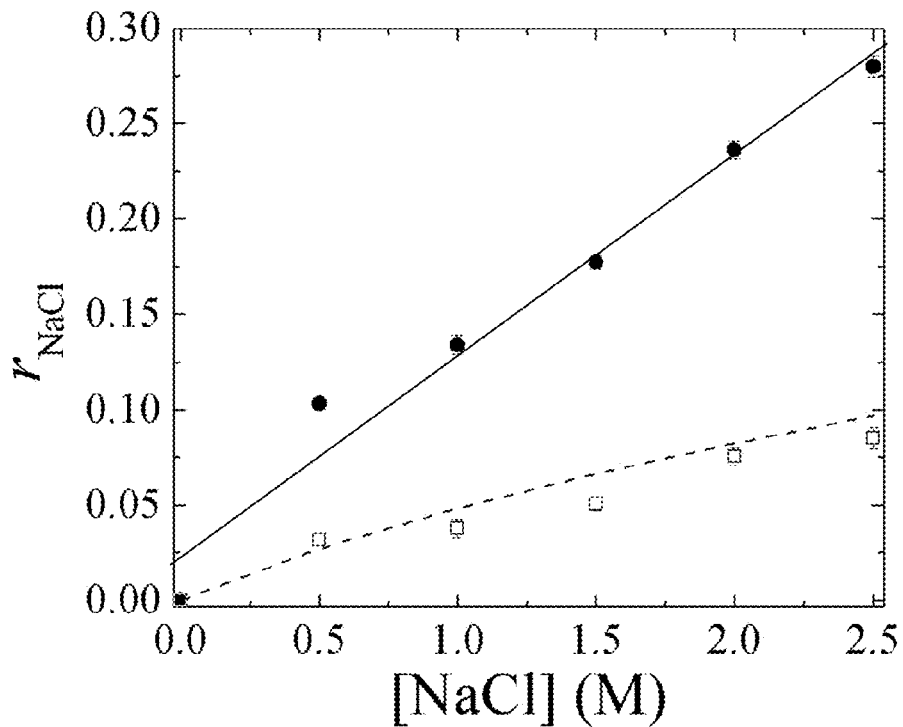
FIG. 10 is a graph depicting experimental NaCl content (●) in a PSS/PDADMA MiPEC. The solid line is a guide to the eye showing an intercept of about 0.023, which is from non-stoichiometric and trapped ions. The theoretical value of $r_{NaCl}$ expected from doping only is shown as a dotted line. When the estimated NaCl content in pore volume, and the non-stoichiometric and trapped ions are subtracted, the remainder (□) is close to NaCl expected from doping. The theoretical value of $r_{NaCl}$ was calculated assuming $K_{dop}=0.27$.

Reviewing FIGS. 6, 7, and 8, the total ion content given by Equation 5 contains contributions from salt in pores, $m_{NaCl,pore}(x)$, salt from doping $m_{NaCl,dop}(x)$ and (sodium) ions from polyelectrolyte non-stoichiometry $m_{Na,nonst}$. The latter does not depend on solution salt concentration. FIG. 10 depicts the NaCl content (the mass of salt normalized by the mass of polymer) versus the solution salt concentration in a PSS/PDADMA MiPEC. Because of the drying method used, all the experimental points include about 1.0% (r=0.01) from trapped NaCl (elemental analysis provided 0.62% Cl which is 1.02% NaCl) and 1.26% (r=0.0126) from the Na$^+$ counterions balancing excess PSS.

The pore content of salt, $r_{NaCl,pore}$, is approximated by $$r_{NaCl,pore} \sim \frac{\text{pore \%}}{100 - \text{pore \%}} \times \frac{58.5}{1000}[NaCl] \quad [10]$$

When this contribution is subtracted from $r_{NaCl}$ in FIG. 10, along with the r=0.023 intercept, the remainder corresponds more closely to the expected salt brought in by doping alone. Samples of MiPEC exhibit informative changes in optical properties when they are immersed in different salt concentrations. A MiPEC prepared in 2.5 M NaCl is clear and transparent after the centrifugation step whereas it turns white and opaque when it is soaked in NaCl solutions of lower concentration. These observations are consistent with a porous structure wherein the refractive index of the doped complex is matched with the solution at high salt concentrations (n is ca. 1.4 for 3M NaCl). See *CRC Handbook of Chemistry and Physics,* 87th ed., Editor-in-Chief: David R. Lide, 2007; CRC Press, Cleveland, Vol. 129. At lower salt concentrations a refractive index difference between pore and complex leads to scattering. Light scattering in hydrogels has been used to track their formation and response. See Kara, S.; Pekcan, O. *Polymer* 2000, 41, 6335-6339; Pekcan, O.; Catalgil-Giz, H.; Caliskan, M. Polymer 1998, 39, 4453-4456; and Zhou, X. J.; Weng, L. H.; Zhang, J. M.; Shen, D. Y.; Xu, J. *J. Polym. Sci. B.* 2003, 41, 2290-2295.

We believe that in the MiPECs studied here, excess PSS appears on the outer surface of the complex and on the inner surface of the pores. Additional PSS resides inside the pores, generating osmotic pressure. When the solution osmotic pressure of the increases, at higher salt concentrations, the excess osmotic pressure of the PSS in the pores is masked and water leaves the MiPEC, as seen in FIG. 9.

Dynamic Mechanical Properties of PSS/PDADMA MiPECs.

Figure 11:
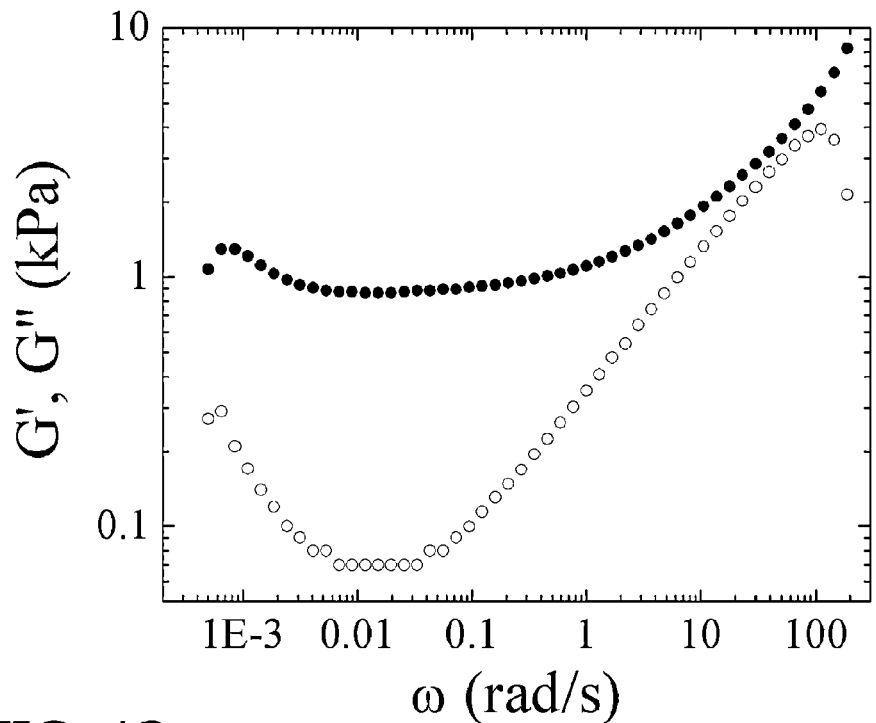
FIG. 11 is a graph depicting the dynamic storage modulus G' (●) and loss modulus G" (○) at 37° C. as function of the angular frequency, ω (rad/s) for a PSS/PDADMA MiPECs in 2.5 M NaCl.

As the mechanical properties of a gel depend on crosslink density, the dynamic mechanical properties of MiPECs were characterized by rheometry in a plate-plate geometry. All samples were mounted in an environmental chamber. The MiPECs were immersed in salt solution of fixed concentration and the temperature maintained at 37° C. G' and G" for a PSS/PDADMA MiPEC exposed to 2.5 M NaCl are shown in FIG. 11.

Although G' and G" decreased at the lowest angular frequencies, no liquid like behavior was observed. At higher frequencies (>10 rad/s) the moduli become similar and increase with the frequency: G'~G"~$\omega^\Delta$ with a $\Delta$≈0.5. In this region, the shortest relaxation processes in the complexes take place. From where G' and G" converge, these relaxations are apparently on the order 10 ms, consistent with stress-relaxation results of PEMUs. See Jaber, J. A.; Schlenoff, J. B. *J. Am. Chem. Soc.* 2006, 128, 2940-2947. At such a time scale, the movement of short chain sections containing only few monomers is feasible. If the crosslink density is low enough, these sections are not sensitive to the network structure. Thus, the behavior of these sections can be described by Rouse's model that predicts: $G'(\omega)=G''(\omega)\ \omega^{1/2}$. See Rouse, P. E. *J. Chem. Phys.* 1953, 21, 1272-1280.

Figure 12:
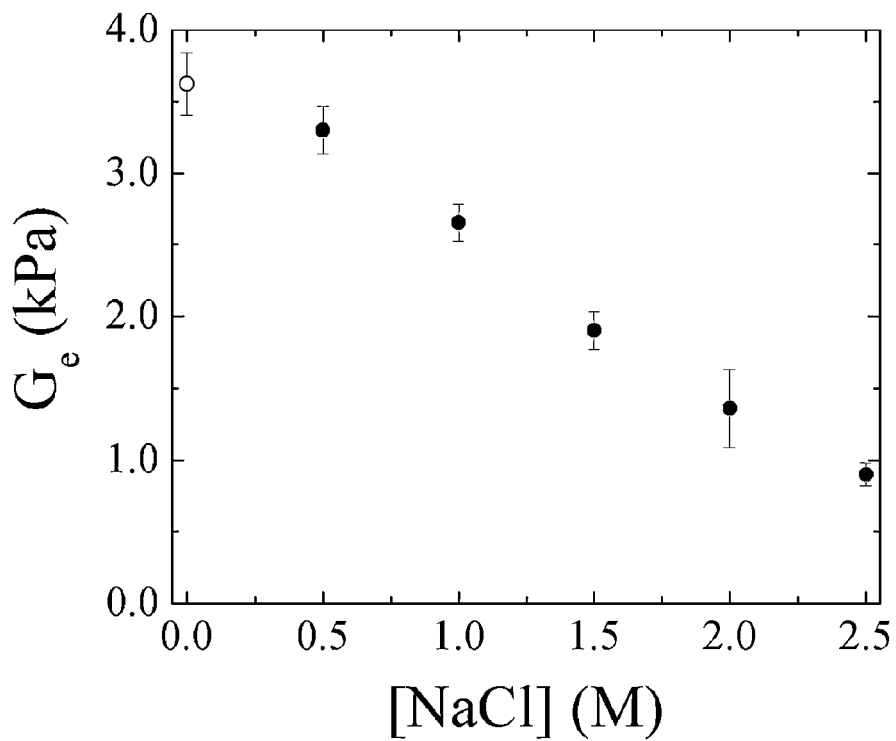
FIG. 12 is a graph depicting equilibrium shear modulus in the rubbery plateau (●), $G_e$ at 37° C. and an angular frequency of 0.003 rad/s for a PSS/PDADMA MiPEC in 0.5 to 2.5 M NaCl solutions. For comparison, the value of G' at 0.003 rad/s for the MiPEC immersed in water (○) is displayed.

At intermediate angular frequencies, between 0.002 and 1 rad/s, the complex exhibits mainly elastic response. G' has a weak frequency dependence and it is significantly greater than G" although the viscous response is not negligible, having a phase angle between 4° and 12°. In this zone, termed the rubbery plateau, G' is constant, equal to the equilibrium shear modulus, $G_e$. It was shown that physical cross-linked gels also follow the rubber elasticity theory of a network,[52] where $G_e$ is described by the following:

$$G_e = \Phi \nu RT \tag{11}$$

where $\Phi$ is a correction factor approaching unity for isotropic systems, $\nu$ the density of elastically active chains which is proportional to the crosslink density, R the ideal gas constant, and T the absolute temperature. $G_e$ is directly proportional to the number of crosslinks in the material. For all salt concentrations, except [NaCl]=0, a rubbery plateau was observed for the PSS/PDADMA MiPEC. $G_e$, taken from the plateau, was used to infer the crosslink density in the material in response to salt concentrations between 0.5 M and 2.5 M using Equation 11. FIG. 12 depicts $G_e$, recorded at 0.003 rad/s, as a function of salt concentration. FIG. 5A also includes G' for the MiPEC in water at this frequency.

$G_e$ decreases with salt concentration. The crosslinks are progressively replaced by counterion-doped sites and the MiPEC becomes softer. In this concentration range, we estimate the crosslink density falls from 72% to 35%. See Jaber, J. A.; Schlenoff, J. B. *J. Am. Chem. Soc.* 2006, 128, 2940-2947. The decrease of $G_e$ is linear in response to the decrease in crosslinks deduced from FIG. 6. This result implies that the change in water content (FIG. 9), which should lead to an increase in modulus, has a minor impact on $G_e$ in comparison to the effect of crosslink density.

Figure 13:
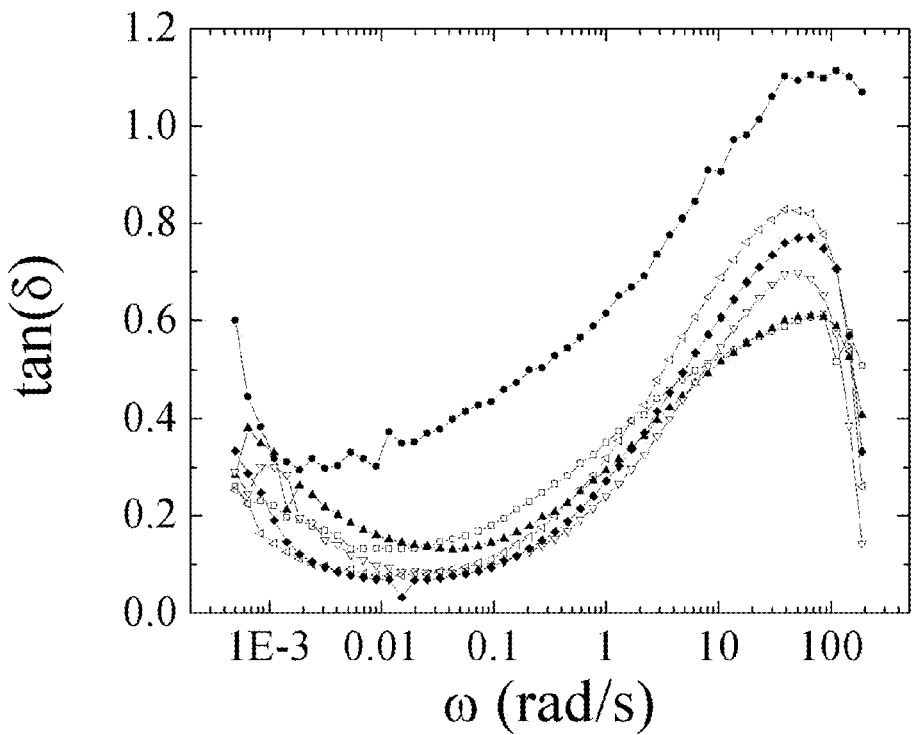
FIG. 13 is a graph depicting tan(δ) as a function of frequency at 37° C. for PSS/PDADMA MiPECs immersed in salt concentrations of 0.0 M (●), 0.5 M (□), 1.0 M (▲), 1.5 M (▽), 2.0 M (♦), 2.5 M (◁).

The salt concentration also influences the loss modulus. Response to salt concentration is weak in the rubbery plateau since the material is essentially elastic but it becomes important at higher frequencies. FIG. 13 summarizes the frequency dependence of tan($\delta$) for all the salt concentrations.

The frequency response is similar for all salt concentrations. FIG. 13 also shows anomalous response in salt-free water, which displays tan($\delta$) value greater than the complexes immersed in NaCl solutions. Two regimes are seen in the behavior of tan($\delta$). At low frequencies (<1 rad/s), the low values of tan($\delta$) are consistent with the presence of a rubbery plateau for all the salt concentrations. At higher frequencies tan($\delta$) increases as the material dissipates energy. The maximum tan($\delta$) values, reached just before entering the non-linear viscoelastic region (characterized by the rapid decrease of tan($\delta$)) increase with increasing NaCl concentration. This characteristic behavior at high frequencies was also observed with PSS/PDADMA multilayers. See Jaber, J. A.; Schlenoff, J. B. *Chem. Mat.* 2006, 18, 5768-5773. Decreasing crosslink density in the complex, whether in the PEMU or MiPEC morphology, provides for better dissipation of energy into the material. Thus, their damping properties can also be controlled by the ionic strength of the surrounding solution. The anomalous properties of the MiPEC in water suggest exceptionally good damping properties over a wide range of frequencies in the absence of salt. Under these conditions, the complex is hyperswollen with water (contains about 80% by weight $H_2O$, see FIG. 9).

Various techniques, none frequency dependent, such as nanoindentation, quartz crystal microbalance or capillary wave experiments on film morphologies and deformation with atomic force microscopy or under osmotic pressure on capsule morphologies have been used to determine the mechanical properties of PEMUs. See Richert, L.; Engler, A. J.; Discher, D. E.; Picart, C. *Biomacromolecules* 2004, 5, 1908-1916; Pavoor, P. V.; Bellare, A.; Strom, A.; Yang, D. H.; Cohen, R. E. *Macromolecules* 2004, 37, 4865-4871; Nolte, A. J.; Rubner, M. F.; Cohen, R. E. *Macromolecules* 2005, 38, 5367-5370; Francius, G.; Hemmerle, J.; Ball, V.; Lavalle, P.; Picart, C.; Voegel, J. C.; Schaaf, P.; Senger, B. *J. Phys. Chem. C* 2007, 111, 8299-8306; Francius, G.; Hemmerle, J.; Ohayon, J.; Schaaf, P.; Voegel, J. C.; Picart, C.; Senger, B. *Microscopy Res. Tech.* 2006, 69, 84-92; and Mermut, O.; Lefebvre, J.; Gray, D. G.; Barrett, C. *J. Macromolecules* 2003, 36, 8819-8824. See Salomaki, M.; Laiho, T.; Kankare, J. *Macromolecules* 2004, 37, 9585-9590; and Lukkari, J.; Salomaki, M.; Aaritalo, T.; Loikas, K.; Loiko, T.; Laiho, T.; Kankare, J. *Langmuir* 2002, 18, 8496-8502. Safouane, M.; Miller, R.; Möhwald, H. *J. Coll. Interfac. Sci.* 2005, 292, 86-92. Dubreuil, F.; Elsner, N.; Fery, A. *Europ. Phys. J. E* 2003, 12, 215-221. Vinogradova, O. I.; Lebedeva, O. V.; Vasilev, K.; Gong, H. F.; Garcia-Turiel, J.; Kim, B. S. *Biomacromolecules* 2005, 6, 1495-1502. Gao, C.; Donath, E.; Moya, S.; Dudnik, V.; Möhwald, H. *Europ. Phys. J. E* 2001, 5, 21-27.

There is a significant difference in the magnitude of moduli for PEMUs found in most of these studies and the G values for MiPECs reported here. Generally, $G_e$ values for multilayers built with classic systems such as PSS/PDADMA or PSS/PAH lie in the range 0.001-1 GPa. For example, we found $G_e$=0.3 MPa for a PSS/PDADMA PEMU in 1 M NaCl (at r.t.) which is almost 3 orders greater than $G_e$ for the same material as a MiPEC in the same salt concentration (at 37° C., FIG. 12). While this difference can be partially explained by the slightly higher temperature, much higher water content and the microporosity of the MiPEC. Comparing FIGS. 9 and 12, it is clear that changes in the extrinsic site concentration (doping) overwhelm effects on $G_e$ due to changes in water content. The 17% excess of PSS effectively introduces a high "baseline" doping level in MiPECs even when they are immersed in pure water. In other words, the excess PSS plasticizes the MiPEC and decreases the crosslink density.

MiPECs of PMAA/PDADMA as Candidates for the Replacement of the Nucleus Pulposus.

Gels with moduli in the range of kPa are of widespread interest as biomaterials. Many native tissues have moduli in this range, including nasal cartilage, the kidney cortex, and the advential layer. See Frank, E. H.; Grodzinsky, A. J. *J. Biomech.* 1987, 20, 629-639; Erkamp, R. Q.; Wiggins, P.; Skovoroda, A. R.; Emelianov, S. Y.; O'Donnell, M. *Ultras. Imag.* 1998, 20, 17-28; and Carter, F. J.; Frank, T. G.; Davies, P. J.; McLean, D.; Cuschieri, A. *Med. Imag. Anal.* 2001, 5, 231-236. MiPECs exhibit properties which fit many of the requirements of materials to replace these tissues. The conditions cannot be tuned by salt concentration, since they must be fixed at physiological (37° C., pH ca. 7 and about 0.15 M NaCl), but the properties of a MiPEC can be matched to those of the tissue by proper selection of composition.

Figure 14:
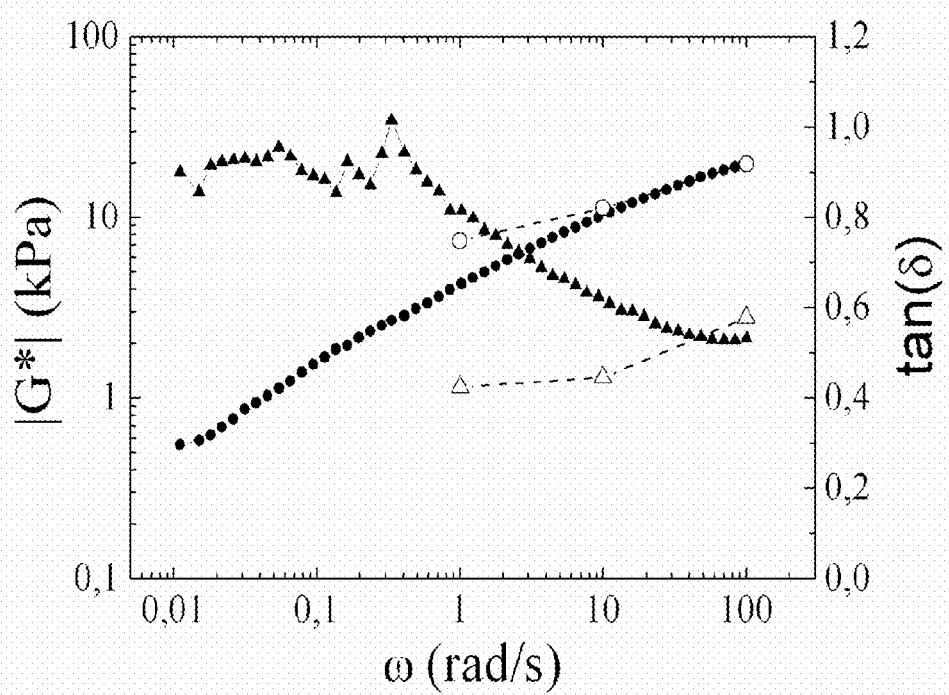
FIG. 14 is a graph depicting the dynamic complex modulus |G*| (●) and the tan of the loss angle (▲) at 37° C. as function of the angular frequency, ω (rad/s) for a PMAA/PDADMA MiPEC made and soaked in 0.15 M NaCl concentration. For comparison, the values of |G*| (○) and tan(δ) (Δ) obtained by Iatridis et al. for a non-degenerated human lumbar nucleus pulposus are also plotted.

The intervertebral disc is composed of a nucleus pulposus surrounded by an annulus fibrosus. The latter is a tough skin while the nucleus pulposus is a softer shock absorbing material with a water content between 70-80% where |G*| from 1 to 100 rad/s lies between 7 and 20 kPa with a loss angle between 23°-30° for in vivo conditions.[27] After experimentation with a few combinations of polycations and polyanions, it was found that MiPECs made from PMAA and PDADMA were suitable for mimicking the properties of the nucleus pulposus. These MiPECs are well doped in 0.15 M NaCl, as are PEMUs of similar composition. The pH was fixed at 7.0 during synthesis and use to maintain the weak acid functionality on PMAA in the ionized state, and the ionic strength was likewise constant at 0.15 M NaCl. The water content of the PMAA/PDADMA MiPEC under these conditions was about 82 wt %. The mechanical properties of this complex, |G*| and tan(δ), are shown on FIG. 14.

The properties are different from the PSS/PDADMA MiPECs. A rubbery behavior is no longer observed. At low frequencies G' and G" are similar and low. However, the complex has a solid like behavior with δ<45°. From 1 to 100 rad/s, values of observed |G*| are close to those determined by Iatridis et al.[27] for the nucleus pulposus in the human intervertebral disc. |G*| is within 3 and 20 kPa. The loss angle is of the same magnitude, but increases to higher values at lower frequencies for the PMAA/PDADMA MiPEC. A small amount of crosslinking may reduce the fluid-like properties of the MiPEC at low frequencies to better match the natural material.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A wound protection system comprising a sealed container containing an aqueous solution and a permanently deformable article, the permanently deformable article comprising polyelectrolyte complex comprising an interpenetrating network of at least one predominantly positively charged polyelectrolyte polymer and at least one predominantly negatively charged polyelectrolyte polymer, the polyelectrolyte complex further comprising a plurality of closed-shell pores,
   wherein said plurality of closed-shell pores is encapsulated in the polyelectrolyte complex and further wherein said plurality of pores have at least one average transverse dimension between about 100 nanometers and about 1000 micrometers, said pores comprise water, and the majority of said pores are non-interconnecting.

2. The wound protection system of claim 1 wherein the pores comprise additional large and/or small molecules and/or particles.

3. The wound protection system of claim 1 wherein the polyelectrolyte complex further comprises healing agents.

4. The wound protection system of claim 1 wherein the polyelectrolyte complex further comprises antirejection agents.

5. The wound protection system of claim 1 wherein the polyelectrolyte complex further comprises antibacterial and/or antiviral agents.

6. The wound protection system of claim 1 wherein the polyelectrolyte complex further comprises growth factors.

7. The wound protection system of claim 1 wherein the polyelectrolyte complex further comprises coagulation agents.

8. The wound protection system of claim 1 wherein the polyelectrolyte complex further comprises anticoagulation agents.

9. The wound protection system of claim 1 wherein the polyelectrolyte complex further comprises anti-inflammation agents.

10. The wound protection system of claim 1 wherein the polyelectrolyte complex further comprises one or more additives selected from the group consisting of metal oxide particles, talc, silicon oxide, zirconium oxide, inorganic minerals, clay minerals, carbon powder, graphite, carbon fibers, carbon nanotubes, polymer fibers, cellulose fibers, metal particles, metal fibers, magnetic nanoparticles and combinations thereof.

11. The wound protection system of claim 1 wherein the pores comprise polyelectrolyte.

12. The wound protection system of claim 1 wherein the negatively charged polyelectrolyte polymer is selected from the group consisting of poly(styrenesulfonic acid) (PSS), poly(2-acrylamido-2-methyl-1-propane sulfonic acid) (PAMPS), sulfonated poly(ether ether ketone) (SPEEK), poly(ethylenesulfonic acid), poly(methacryloxyethylsulfonic acid), their salts, and copolymers thereof; polycarboxylates such as poly(acrylic acid) (PAA) and poly(methacrylic acid), polyphosphates, polyphosphonates, and combinations thereof.

13. The wound protection system of claim 1 wherein the positively charged polyelectrolyte polymer is selected from the group consisting of poly(diallyldimethylammonium chloride) (PDADMA), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), including poly(N-methyl-2-vinylpyridinium) (PM2VP), other poly(N-alkylvinylpyridines), and copolymers thereof; protonated polyamines such as poly(allylaminehydrochloride) (PAH) and polyethyleneimine (PEI); polysulfoniums, polyphosphoniums, and combinations thereof.

14. The wound protection system of claim 1 wherein at least one of the polyelectrolytes is selected from the group consisting of proteins, polypeptides, enzymes, DNA, RNA, alginic acid, glycosaminoglycans, proteoglycans, chitosan, chitosan sulfate, cellulose sulfate, polysaccharides, dextran sulfate, carrageenin, guar, sulfonated lignin, polyglycolic acid carboxymethylcellulose and salts thereof.

15. The wound protection system of claim 1 wherein the polyelectrolytes of the article further comprise hydrogen bonding repeat units.

16. The wound protection system of claim 1 wherein the interpenetrating network has an equilibrium shear modulus greater than 1 kPa at 25° C. when immersed in a solution of 0.15 M NaCl in water.

17. The wound protection system of claim 1 wherein the interpenetrating network has an equilibrium shear modulus between about 1 kPa at 25° C. and about 300 MPa when immersed in a solution of 0.15 M NaCl in water.

18. A method of treating a wound, the method comprising:
   activating an article comprising a polyelectrolyte complex comprising an interpenetrating network comprising at least one predominantly positively charged polyelectrolyte and at least one predominantly negatively charged polyelectrolyte, wherein the polyelectrolyte complex further comprises a plurality of closed-shell pores, said plurality of closed-shell pores is encapsulated in the polyelectrolyte complex, and the plurality of pores having at least one average transverse dimension between about 100 nanometers and about 1000 micrometers, and further wherein said activating comprises a process selected from the group consisting of heating said article, increasing an internal salt concentration within said article from a first salt concentration to a second salt concentration wherein the second salt concentration is higher than the first salt concentration, and changing an internal pH of said article; and applying the activated article to the wound.

19. The method of claim 18 wherein the article is contained with a sealed container, the sealed container further comprising an aqueous solution.

20. The method of claim 19 wherein the aqueous solution further comprises at least one charged salt or charged organic molecule.

21. The method of claim 19 wherein said activating occurs prior to breaking the seal.

22. The method of claim 18 wherein activation is performed by heating the article.

23. The method of claim 22 wherein the heating is performed by microwave irradiation, by an exothermic chemical reaction or mixing, or by induction heating.

24. The method of claim 18 wherein activation is performed by adding a salt.

25. The method of claim 18 wherein the activation is performed by changing the pH.

26. The method of claim 18 further comprising wrapping the hydrated, activated article circumferentially around a damaged limb, vessel, nerve, or bone and sealing the network back on itself.

27. The method of claim 18 wherein the interpenetrating network has an equilibrium shear modulus greater than 1 kPa at 25° C. when immersed in a solution of 0.15 M NaCl in water.

28. The method of claim 18 wherein the interpenetrating network has an equilibrium shear modulus between about 1 kPa at 25° C. and about 300 MPa when immersed in a solution of 0.15 M NaCl in water.

29. A polyelectrolyte complex comprising an interpenetrating network of at least one predominantly positively charged polyelectrolyte polymer and at least one predominantly negatively charged polyelectrolyte polymer, wherein the polyelectrolyte complex has equilibrium shear modulus between about 1 kPa and about 300 MPa at 25° C. when immersed in a solution of 0.15 M NaCl in water and further wherein the polyelectrolyte complex further comprises a plurality of closed-shell pores, the plurality of pores having at least one average transverse dimension between about 100 nanometer and about 1000 micrometers.

30. The polyelectrolyte complex of claim 29 further comprising an additive selected from the group consisting of a healing agent, an antiviral agent, a growth factor, an anticoagulation agent, a coagulation agent, paclitaxel, and any combination thereof.

* * * * *